US012601667B2

(12) United States Patent
Crandall et al.

(10) Patent No.: US 12,601,667 B2
(45) Date of Patent: Apr. 14, 2026

(54) AUTOMATED TURF TESTING APPARATUS AND SYSTEM FOR USING SAME

(71) Applicant: Biocore LLC, Charlottesville, VA (US)

(72) Inventors: Jeff Crandall, Charlottesville, VA (US); Edward Meade Spratley, Charlottesville, VA (US); Philipe Aldahir, Chattanooga, TN (US); Zack Sutton, Fort Collins, CO (US); Steven Sutton, Fort Collins, CO (US)

(73) Assignee: BIOMECHANICS CONSULTING AND RESEARCH, LLC, Charlottesville, VA (US)

( * ) Notice: Subject to any disclaimer, the term of this patent is extended or adjusted under 35 U.S.C. 154(b) by 496 days.

(21) Appl. No.: 18/075,952

(22) Filed: Dec. 6, 2022

(65) Prior Publication Data

US 2023/0096232 A1 Mar. 30, 2023

Related U.S. Application Data

(60) Continuation of application No. 17/509,422, filed on Oct. 25, 2021, now Pat. No. 12,474,246, which is a division of application No. 17/192,752, filed on Mar. 4, 2021, now Pat. No. 11,154,244.

(60) Provisional application No. 62/985,126, filed on Mar. 4, 2020.

(51) Int. Cl.
| | |
|---|---|
| *G01N 3/32* | (2006.01) |
| *G01N 3/00* | (2006.01) |
| *G01N 3/08* | (2006.01) |
| *A61B 5/00* | (2006.01) |

(Continued)

(52) U.S. Cl.
CPC ................. *G01N 3/32* (2013.01); *G01N 3/00* (2013.01); *G01N 3/08* (2013.01); *A61B 5/1038* (2013.01); *A61B 5/6807* (2013.01); *G01N 19/02* (2013.01)

(58) Field of Classification Search
CPC .. G01N 3/32; G01N 3/00; G01N 3/08; G01N 19/02; G01N 33/008; G01N 33/24; A61B 5/1038; A61B 5/6807; G01L 5/0033; G01L 5/0042
See application file for complete search history.

(56) References Cited

U.S. PATENT DOCUMENTS

| | | | |
|---|---|---|---|
| 5,259,236 A | 11/1993 | English | |
| 10,333,265 B2 * | 6/2019 | Tong | ..................... H01S 5/4012 |

(Continued)

FOREIGN PATENT DOCUMENTS

| | | |
|---|---|---|
| JP | H0221240 A | 1/1990 |

OTHER PUBLICATIONS

Application No. PCT/US2021/020917, European Search Report dated Feb. 15, 2024.

(Continued)

*Primary Examiner* — Henok Shiferaw
*Assistant Examiner* — Woo C Rhim
(74) *Attorney, Agent, or Firm* — Woods Rogers Vandeventer Black PLC; Nathan A. Evans

(57) ABSTRACT

An apparatus and method for inspection of at least one of grass, artificial turf, infill, or dirt, on a surface, using optical photographic images from a camera and three-dimensional ("3D") depth scans using the camera and one or more laser, to create a mask to distinguish aspects of the surface, so that the surface can be measured and analyzed.

24 Claims, 35 Drawing Sheets

Fiber Color Analysis

Full Image Color Palette

Isolated Fiber Color Palette

(51) Int. Cl.
  *A61B 5/103* (2006.01)
  *G01N 19/02* (2006.01)

(56) References Cited

U.S. PATENT DOCUMENTS

| | | | | |
|---|---|---|---|---|
| 2006/0217886 | A1 * | 9/2006 | Fujimoto | G08B 13/19652 |
| | | | | 701/96 |
| 2012/0297889 | A1 | 11/2012 | Yngve | |
| 2013/0055797 | A1 * | 3/2013 | Cline | G01N 3/303 |
| | | | | 73/82 |
| 2014/0168633 | A1 * | 6/2014 | Guetta | G08B 13/189 |
| | | | | 356/5.01 |
| 2015/0096276 | A1 * | 4/2015 | Park | A01D 34/008 |
| | | | | 56/10.2 A |
| 2017/0084193 | A1 * | 3/2017 | Togasaka | G06T 7/70 |
| 2019/0320580 | A1 * | 10/2019 | Haneda | A01D 34/008 |
| 2020/0141729 | A1 * | 5/2020 | Nishita | G01S 17/66 |
| 2020/0150250 | A1 * | 5/2020 | Boyraz | G01S 7/4802 |
| 2021/0000006 | A1 * | 1/2021 | Ellaboudy | A01B 69/001 |
| 2021/0063578 | A1 * | 3/2021 | Wekel | G01S 17/894 |
| 2021/0073959 | A1 * | 3/2021 | Elmalem | G06N 3/084 |
| 2021/0100166 | A1 | 4/2021 | Becke et al. | |
| 2021/0165100 | A1 * | 6/2021 | Ramsteiner | G01S 17/931 |
| 2021/0275099 | A1 | 9/2021 | Crandall et al. | |
| 2023/0096232 | A1 * | 3/2023 | Crandall | G01L 5/0042 |
| | | | | 73/866 |
| 2023/0211378 | A1 * | 7/2023 | Sørensen | G01N 15/0272 |
| 2025/0072412 | A1 * | 3/2025 | Fu | A01G 25/09 |

OTHER PUBLICATIONS

Application No. PCT/US23/82781, International Search Report and Written Opinion dated Apr. 19, 2024.

* cited by examiner

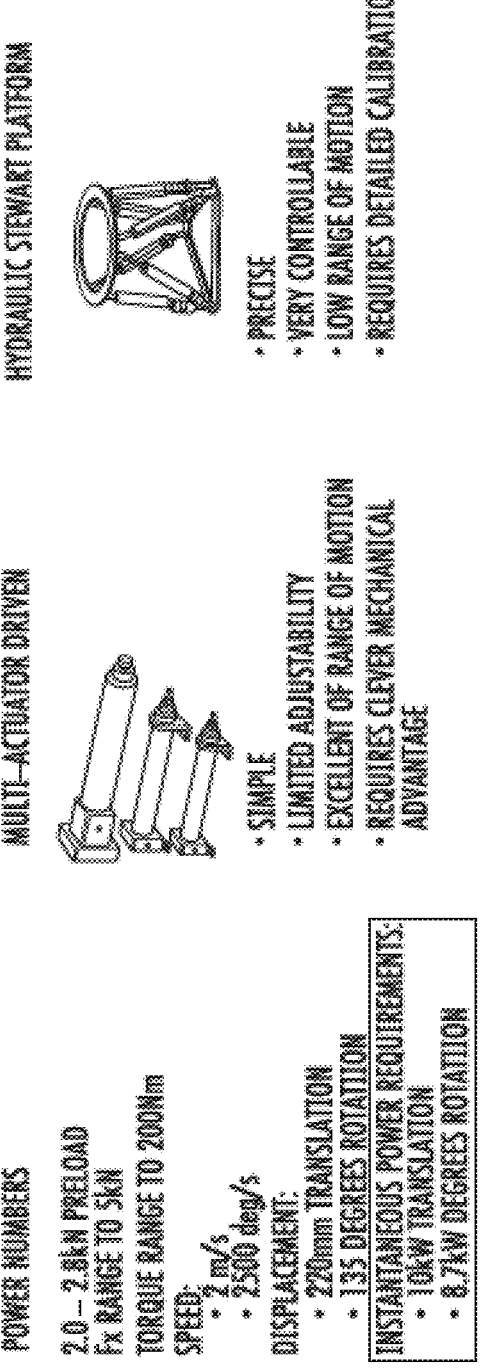

FIG. 10

HYDRAULIC STEWART PLATFORM

- PRECISE
- VERY CONTROLLABLE
- LOW RANGE OF MOTION
- REQUIRES DETAILED CALIBRATION

MULTI-ACTUATOR DRIVEN

- SIMPLE
- LIMITED ADJUSTABILITY
- EXCELLENT OF RANGE OF MOTION
- REQUIRES CLEVER MECHANICAL ADVANTAGE

POWER NUMBERS 2.0 – 2.8kN PRELOAD
Fx RANGE TO 5kN
TORQUE RANGE TO 200Nm
SPEED:
- 2 m/s
- 2500 deg/s
DISPLACEMENT:
- 220mm TRANSLATION
- 135 DEGREES ROTATION
INSTANTANEOUS POWER REQUIREMENTS:
- 10kW TRANSLATION
- 0.7kW DEGREES ROTATION FIGURE 15 – Shaft Actuation Assembly FIGURE 16 – Shaft Actuation Assembly – Cross-section FIGURE 17 – Shaft Bearing Assembly – SIDE Footform – ISO

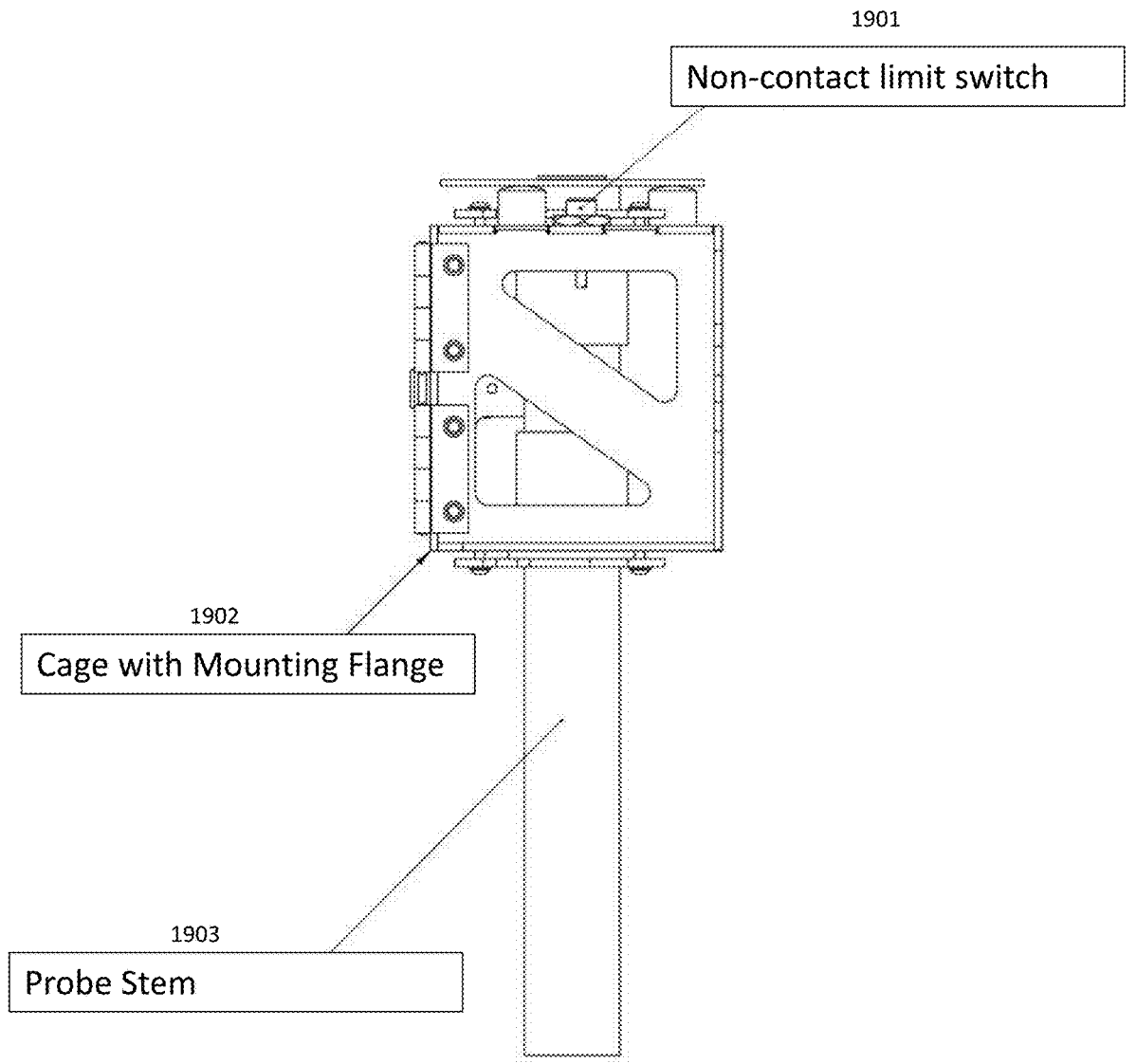
1901
Non-contact limit switch
1902
Cage with Mounting Flange
1903
Probe Stem
FIGURE 19 – Turf Datum Finder – SIDE Impact Tester & Consolidated Data Capture – Automated by
Solenoid

Actuation Architecture

Controller States
* 11 Controller States
* Lights
  * Red blocks = flashing red
  * Green blocks = solid green
  * E-stop = flashing red and green
* Work to complete
  * Add cable preload states

FIGURE 22 - Device Control Diagram

FIGURE 23 – Device Power Architecture

Fiber Color Histogram

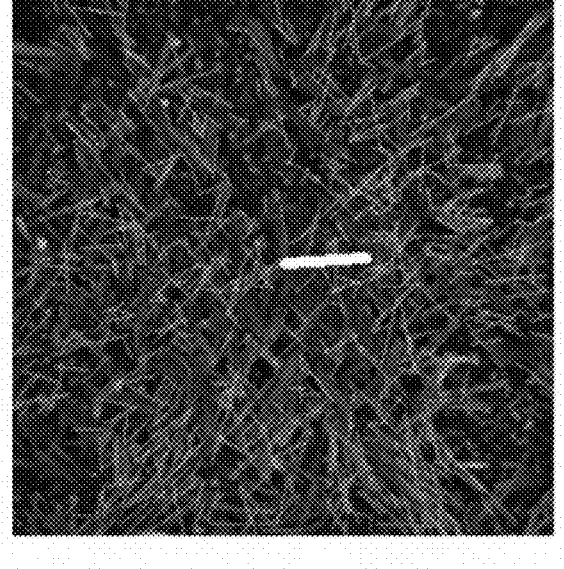
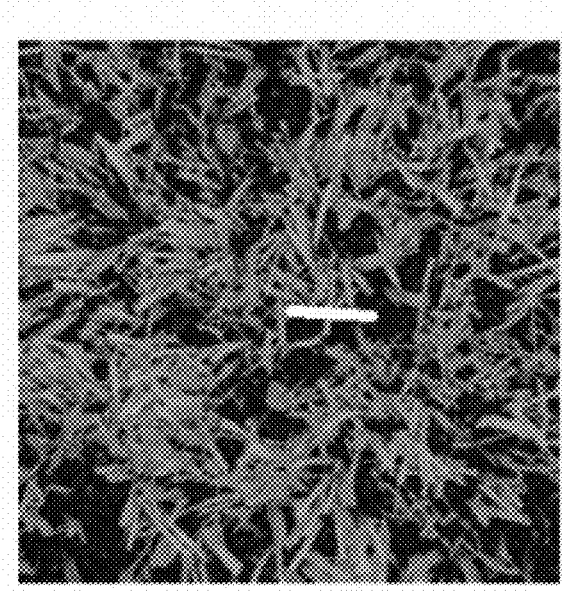
Fiber lay analysis (WIP)
FIGURE 27

Fiber lay analysis (WIP)

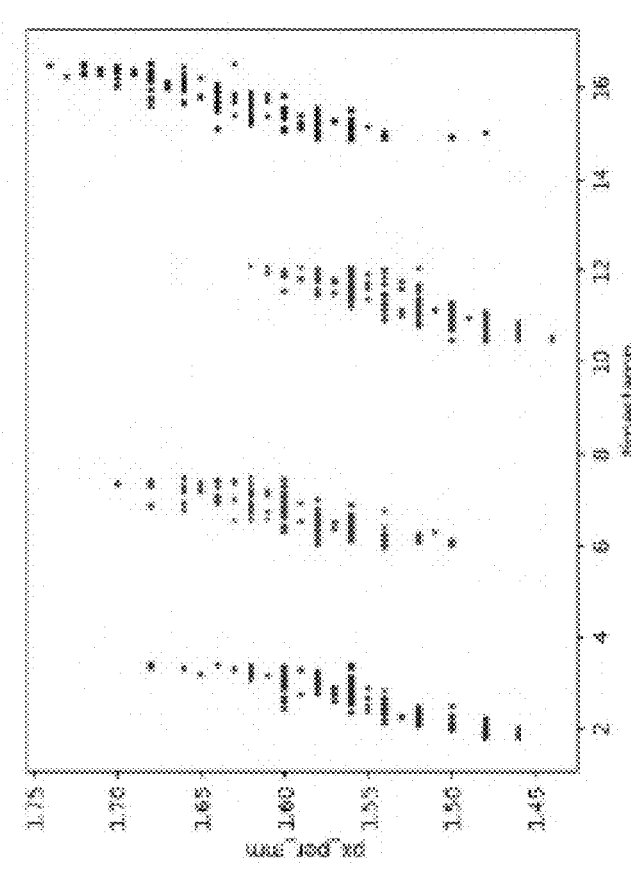
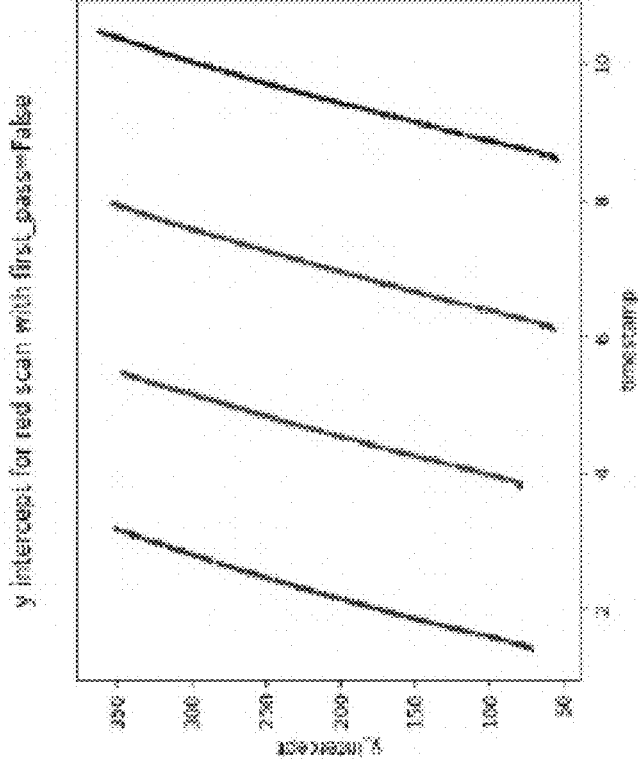
FIGURE 34

AUTOMATED TURF TESTING APPARATUS AND SYSTEM FOR USING SAME

CROSS-REFERENCE TO RELATED APPLICATIONS

The present application is a continuation of and relies on the disclosures of and claims priority to and the benefit of the filing dates of U.S. application Ser. No. 17/509,422, filed Oct. 25, 2021, and Ser. No. 17/192,752, filed Mar. 4, 2021 (now U.S. Pat. No. 11,154,244), and U.S. Provisional Application No. 62/985,126, filed Mar. 4, 2020, which are incorporated by reference herein in their entireties. Information from the following related website is also hereby incorporated by reference in its entirety: https://www.figma.com/proto/PeRRW6ZRPMwgMkVAZ4n6yl/BEAST-UI?node-id=4%3A11&viewport=9974%2C-566%2C0.7194263339042664&scaling=min-zoom

BACKGROUND OF THE INVENTION

Field of the Invention

The present invention relates to a mobile apparatus and associated system that is completely or partially automated and is configured, in aspects, to measure sport surface (e.g., sport turf) characteristics and the safety of athletic apparel accurately and consistently in an apparel-to-surface interaction, in a manner that is quantifiable and repeatable. This application uses sport turf as an example but is not limited to sport turf, because the invention can be used with non-grass and non-turf surfaces using an appropriate foot form, instrumentation, and/or loads and motions particular to a certain sport (e.g., tennis, baseball, football, soccer, and so on). In examples only, sport turf is considered to be a naturally or artificially grassed surface and the immediate underlying environment, managed and prepared for fast and aggressive playing such as in American Football and Soccer. With reliable gameday, practice, or other data, causes and dangers of injury on natural or synthetic turf, using particular athletic apparel that interact with the turf can be better understood, predicted, and reduced through better field and apparel characterization and rating(s). Moreover, as described herein, the shoe/surface interaction contributes to athletic performance, which, according to the present invention, could also be better characterized, understood, predicted, and even enhanced.

Accurately and consistently quantifying turf conditions, as well as the effect of turf conditions on athletic apparel in situations and conditions that mimic athletic movement, can be used to reduce athletic injury occurrences, improve player performance, establish accurate, independent standards for artificial turf manufacturing, installation, and maintenance, prevent expensive stadium rework, and can lead to standardizing field and turf assessments across sports fields, including but not limited to American football and soccer, just to name a couple examples. With the instrumentation, system, products and methods described herein, and a sport-specific foot form, these tests could be performed on clay surfaces (e.g., baseball skins, warning track, tennis courts), hard surfaces (e.g., tennis, pickleball, volleyball, basketball), sand surfaces (e.g., beach volleyball, bocce, horse tracks), and other grassed (artificial or natural) surfaces such as horse tracks and cricket fields/pitches. With the present invention's instrumentation, the apparatus and system could also be used to quantify performance of a golf club or surface by characterizing a club to ground interaction, including an interaction that results in a portion of the playing surface being removed by the club head. Such testing may also be used in non-athletic environments where synthetic or natural surfaces are utilized. In order to accomplish adequate testing for quantifying turf conditions and effects of athletic apparel, the apparatus taught herein uses not only horizontal and vertical forces, but also torsional forces, and all three forces in combination at the same or different times. Thus, the apparatus and system can apply horizontal, vertical, and torsional forces, and link these forces together and combine them into a single motion to more closely mimic behavior of, for example, a human foot, leg, or entire body during an athletic movement, thereby applying and measuring interactions between all three forces at the same or different times.

Further, in embodiments, the system can be a platform for developing three-dimensional ("3D") scanning and analysis techniques for turf and natural grass fields, among other possible scan targets. The different elements that make up the platform can expose universal, abstract interfaces so that new controllers, cameras, location systems, etc., can be switched in, swapped, or replaced at a later time. The analysis provided is, in aspects, meant to comprise expert-level analysis of every step of the process. The data provided can represent a host of introspective data so that the platform can diagnose issues or problems with the turf, fibers, grass, or in-fill. Knowing the data means the quality of the turf/grass/fibers/in-fill can be improved, thereby improving safety, aesthetics, or other parameters of the analyzed turf/grass/fibers/in-fill.

The system, in aspects, can be referred to as a mixed optical-depth estimation for field analysis that combines 3D surface scanning with optical images. The depth and optical data can be used together for more robust, height-aware, and color-aware measurements. Using the techniques described herein, a user can apply different kinds of data as filters in order to determine fiber height, infill evenness, grass coverage, fiber color, fiber wear, grass color, and more. In aspects, several industrial lasers, geared stepper motors, and one or more first-surface mirror are configured in a flat arrangement. In aspects, the camera that takes the optical image can also take the scan, and can therefore stitch them the images and/or scans substantially seamlessly. In aspects, the lasers can scan across the target at an angle so that the height of the target is shown as a divergence from the laser line to the camera.

Description of Related Art

In the National Football League ("NFL"), for example only, there is a significantly higher rate of non-contact injuries to lower limbs on synthetic turf than on natural turf (i.e., 28-69% higher). There have been ongoing attempts to determine why this is, however, the results are inconclusive. This suggests that the data currently being collected can be improved upon. Currently, typically before every game, the turf is manually inspected, and the data is recorded for reference if an injury were to occur.

While current on-field tests include impact hardness, infill depth and evenness, soil moisture content, surface shear resistance using a shear vane, percentage ground cover, visual inspection, and stability rating (post-game), the current tests have proven to be inconsistent, non-comprehensive, and subjective. Injuries continue to be a problem in all sports despite currently available safeguards, and a need exists for an improved way to attempt to decrease athletic injuries across all sports, especially those played on turf.

SUMMARY OF INVENTION

Due to the current limitations, it is an object of the current invention to allow for data collection on, for example, shoe-to-turf interaction while subject to applied forces in order to properly correlate injury to turf characteristics, and/or characteristics of the cleat or shoe. In aspects, data collection might include, for example, kinetic and kinematic data during the shoe-turf interaction, measurement of turf characteristics through additional measuring devices, and recording of characteristics of the shoe and/or turf used for the shoe-turf interaction test. Because of the capabilities of the current invention, when injuries occur, the incidence of injury can be traced back to the turf data or apparel data collected by the inventive apparatus and compared amongst other cases of injury or, alternatively, with cases of non-injury. Once common injury metrics or injury risks are established, by way of example only, mechanical parameters measured can be minimized in the manufacture of turf or athletic apparel, thereby reducing injuries based on quantifiable data. To accomplish this, the current invention is, in aspects, mobile and completely- or partially-automated, and configured to provide reliable data that is repeatable and reproducible.

It is an object of the current invention to test the safety of artificial or natural turf and/or athletic apparel, especially shoes including but not limited to cleats, using a shoe-surface tester that determines and analyzes the mechanical interactions between shoes and an athletic playing surface/turf and performs other measurements commonly taken on turf, and/or determines and analyzes whether the shoes and/or playing surface are up to standards and/or deemed safe for athletic events. The device simulates and measures shoe-to-turf interactions at loads and rates created or generated by athletes during performance up to and including those deemed to be injurious. This involves measuring displacement, velocity, and acceleration components of the shoe and/or foot form in all directions, as well as in rotation, and any combination of these forces at the same or different times. The apparatus may apply or measure all components (dx, dy, dz, rx, ry, rz) of six degrees of freedom forces and moments of the shoe and or foot form.

The apparatus may use a foot form connected to a system of nested frames or a Stewart platform to accomplish this. Thus, the cleat is actuated through its prescribed load or positional path by a mechanism capable of imparting and withstanding the significant forces and moments without unwanted mechanical deformation, friction, or fatigue that might otherwise influence the data collected. The apparatus or related system is not required to use a foot form or necessarily to measure or analyze a playing surface as it relates to interaction with a foot, cleat, or other playing apparel. For example, in embodiments, the device may also automate or assist with:

a) Computer-aided visual inspection of the surface using high-speed (e.g., by way of example only, around 500 fps) camera(s) aided through machine learning visual recognition technologies with data synchronization, as well as photographic inspection of the surface before and/or after the test to identify foreign objects, quality of the artificial or natural turf, measure ground cover of natural turf, or perform other analyses such as surface evenness or grass coverage/density.

b) Measurement of Energy absorption and rebound/return through measurement of acceleration of a mass or mass-spring system dropped onto turf, through an on-board data collection system, and reporting of this data to the user.

c) Measurement of surface hardness (e.g., Head Injury Criterion measure; Gmax acceleration metric), using devices specified in ASTM F1702 and/or ASTM F355 or other drop test standards, collected through an on-board data collection system, and reporting of this data to the user.

d) Depth measurement (e.g., infill depth and/or evenness);

e) Assessment of Surface stability using, for example, surface shear resistance through the use of a connected shear vane;

f) Detection of Turf moisture levels;

g) Measurement of environmental factors, such as air temperature, ground temperature, air humidity, or other factors;

h) Characterization of Field maintenance; and/or i) Measurement of the top surface of the turf, relative to a datum on the invention, and reporting of that info back to the data collection system.

It is a further object of the current invention to fully characterize turf in a way sufficient to direct changes to the turf and/or shoes for improved performance and/or injury prevention. This mechanism will incorporate all or part of the tests in a controlled manner. By actuating test modes, the system can rely on the data being consistent across stadiums as human-to-human variability inherent in testing with manually powered devices is removed from the process. For example, the system may automatically restrict or fix degrees-of-freedom as appropriate for the desired test mode. The system may also automatically raise or lower the footform for the test, as appropriate. The system may also incorporate locational measurements of the top surface of the test surface into test actuation or data processing. To maintain safety, the system may display the current "state" of the system (for example, whether the system is safe for manual operations or ready to complete a test).

In other embodiments, tests that can be automated are, by way of example only, surface hardness and/or energy absorption and/or return, infill depth and evenness, soil moisture content, surface shear resistance, and/or percentage ground cover detection. In addition to actuating tests, this improved system will also have temperature, pressure, and humidity sensors.

Finally, the device can utilize a translation-rotation footform that can be shod with various footwear that in turn can engage with the ground to analyze shoe or cleat release dynamics.

The foot-form is representative of an athlete's foot in a cleat or shoe and is interchangeable for customizability. This extremity may have roll, pitch, and yaw adjustability to collect data on varying cleat-to-turf interface angles, as well as allow adjustment in the angle of the "toe" of the footform relative to the rest of the footform to approximate flexion of the foot about the MTP joint, yet hold these adjustments fixed in a static pose while testing is occurring. This end effector will be attached to its translation and rotation actuation mechanism via a multi-axis load cell, in aspects. This load cell will collect force and moment data on the foot-form as it moves relative to the turf via, for example, a data acquisition unit. The data collector, such as a computer, will also be recording data from rotational and translational displacement sensors to detect linear position and velocity of the shoe as well as angular rotations and velocities of the shoe. Accelerations of the foot-form may also be measured to either characterize the interaction of the shoe with the turf or, alternatively, to allow characterization of the inertial effects of the device during testing.

In other embodiments, the invention described herein is an apparatus configured to apply controlled horizontal and vertical forces and rotational moments to an end effector (footform) as prescribed, wherein the applied forces and moments mimic a behavior of a human foot or other body part during an athletic movement or reflect forces and/or moments associated with injury and/or performance of a subject's foot or other body part (e.g., the loads generated by football players in the NFL), wherein applying and measuring interactions between prescribed forces, rotational moments, and rotational and linear displacements allows for a safety and/or performance evaluation of a subject, athletic apparel, or an athletic playing surface.

In another embodiment, the invention described herein is an apparatus configured to apply controlled horizontal, vertical, and/or rotational displacements to an end effector (footform) as prescribed, wherein the applied displacements mimic a behavior of a human foot or other body part during an athletic movement or reflect displacements associated with injury and/or performance of a subject's foot or other body part (e.g., motion profiles resulting from athletic tasks resulting in foot/surface interaction during football playing), wherein applying and measuring interactions between prescribed forces, rotational moments, and rotational and linear displacements allows for a safety and/or performance evaluation of a subject, athletic apparel, or an athletic playing surface.

BRIEF DESCRIPTION OF THE DRAWINGS

The accompanying drawings illustrate certain aspects of embodiments of the present invention and should not be used to limit the invention. Together with the written description the drawings explain certain principles of the invention.

FIG. 10 is a depiction of various aspects of the apparatus for athletic apparel and turf testing, according to one embodiment of the present invention.

FIG. 19 is a depiction of the apparatus for athletic apparel and turf testing, including labeled aspects comprising parts of the apparatus, according to one embodiment of the present invention.

FIG. 27 is a depiction showing a fiber lay analysis (WIP) according to aspects of the current invention.

FIG. 34 shows charts according to aspects of the current invention.

DETAILED DESCRIPTION OF INVENTION

Figure 1:
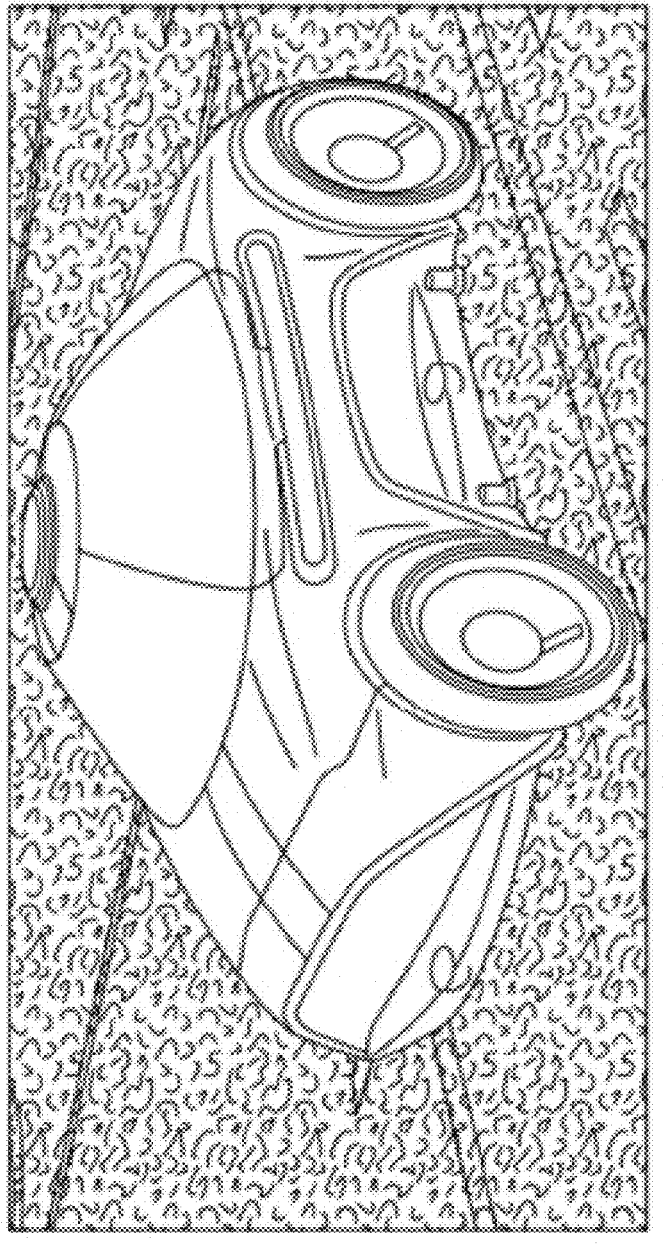
FIG. 1 is a depiction of the apparatus for athletic apparel and turf testing, according to one embodiment of the present invention.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

The present invention can be described in terms of, for example, a foot-form assembly that is preloaded into the ground or turf sample via a tunable vertical load actuator. The apparatus and associated system can impose a constant and/or dynamic or variable horizontal force (and/or rotational torque) on the foot-form assembly while collecting motion profile data on the cleat/shoe as it engages and releases from the turf. In addition to measurement of the displacements associated with applied forces, the system is also capable of logging the minimum required force required to achieve such release from the turf fibers, infill, and overall construction. The minimum force required for cleat/shoe motion relative to the turf matters because this value potentially represents the forces that a player's leg or other body part will experience when loaded in a similar manner to an athlete representative system. This data, along with existing tests results (which will be automated, in aspects), will all be recorded and saved, in aspects. This data can be used to identify the differences in quality of synthetic turf, and the quality of athletic apparel, during injury (or non-injury) compared to the characteristics of natural turf, synthetic turf, non-injury situations, and/or safer or less safe athletic apparel. In addition to data collected during the shoe-turf interaction test, characteristics of the shoe or turf used for the test can be saved and linked with the test data.

The current invention allows for closed-loop control, wherein the system is capable of monitoring force or torque being applied and controlling the force or torque in order to, in aspects, maintain a constantly applied force or torque in a controlled and constant manner. However, in aspects, the apparatus does not necessarily need to provide force or torque in a constant manner and situations may arise where force or torque will not be applied in such a manner; rather the applied force or torque will be variable and/or adjustable. In aspects, the system measures impedance, such that it applies displacement or velocities and measures forces/ torques, for example. The system may also apply and measure admittance, therein applying a force/torque and measuring displacement or velocity; thus, the system may be configured to apply a particular force/torque in order to measure the impact on, for example, an athletic shoe, a human body or body part, and/or real or synthetic turf.

In some instances, the system will use prior data knowing what forces or torques typically, usually, or sometimes cause injury in order to maintain input force/torque applied by the apparatus to determine displacement or movement of a shoe, in aspects, for a given shoe-to-turf combination(s). In embodiments, this may result in a rating or ranking of a shoe and/or turf; in aspects, it can be a pass/fail test, meaning a determination is made whether an athlete can use a particular shoe or not (is it safe, or less safe, or is it unsafe?). Also, based on test results with a given cleat, shoe or generic representation of a shoe-turf interface, the system can verify condition and maintenance of a field, e.g., within tolerances.

In aspects, the current invention tests mechanical interactions between the cleat- or shoe-to-turf interface using a translation test and a rotation test, and force and motion data are recorded via data acquisition, and therefore the system is capable of recording accurate and repeatable results. In aspects, the apparatus is configured to collect on-field displacement, velocity, force and torque data, record impact hardness, measure infill (turf), analyze surface stability (grass), read surface moisture content, perform visual inspection (e.g., via camera or drone), and/or upload or download data manually or automatically.

In aspects, the apparatus processes and displays data tailored for a certain target audience. In aspects, there might be some "hard-coded" data with some data analysis built in locally, remotely, or on a server. In another example, the analysis may be performed online via analysis of metadata stored in a server.

The system is capable of objectively scoring surfaces and footwear, and evaluating geographical compliance of a surface with a standard or protocol (using, for example, GPS to evaluate an entire field area or a portion of a field area and recommending localized intervention/maintenance).

Figure 3:
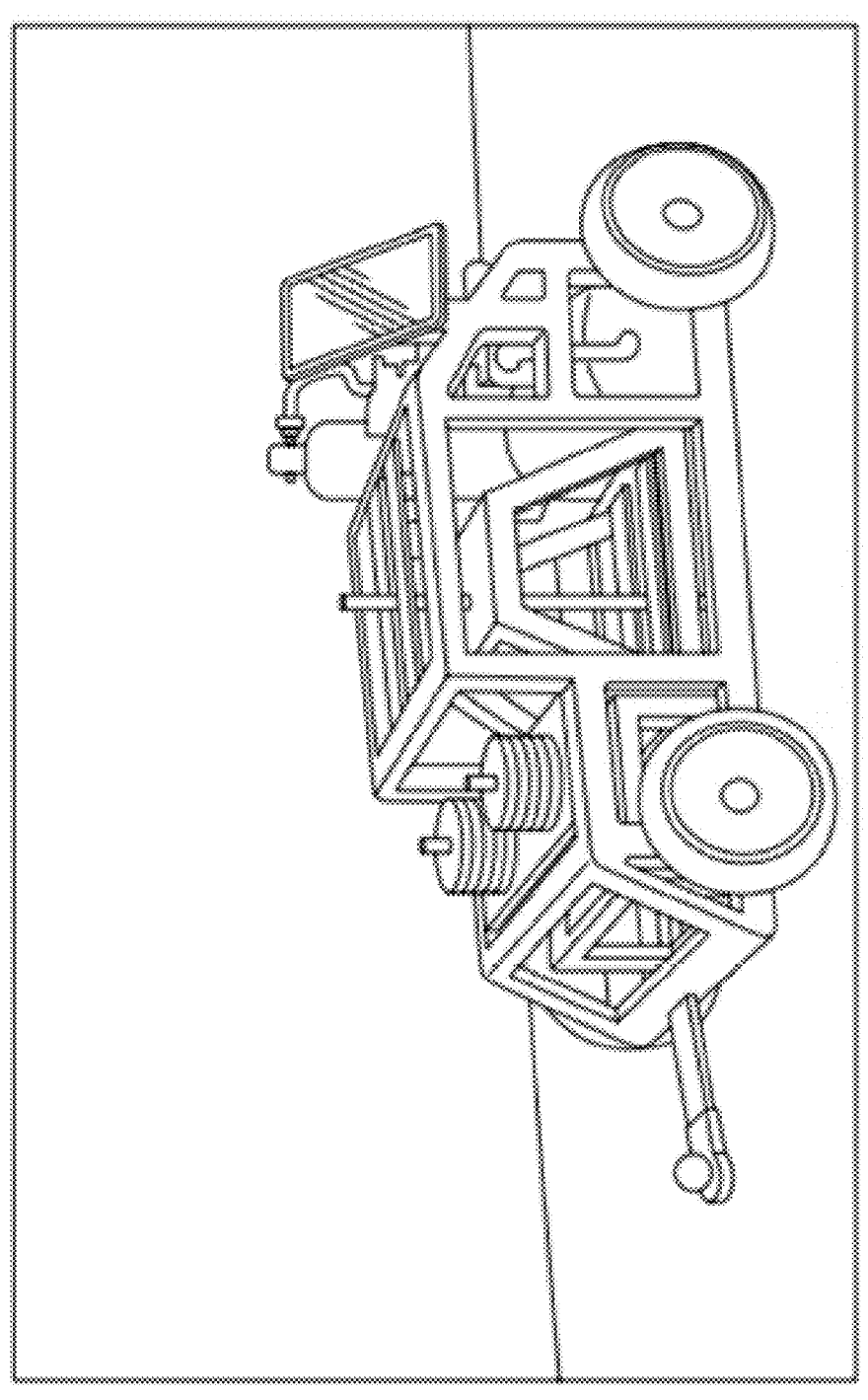
FIG. 3 is a depiction of the apparatus for athletic apparel and turf testing, according to one embodiment of the present invention.
Figure 4:
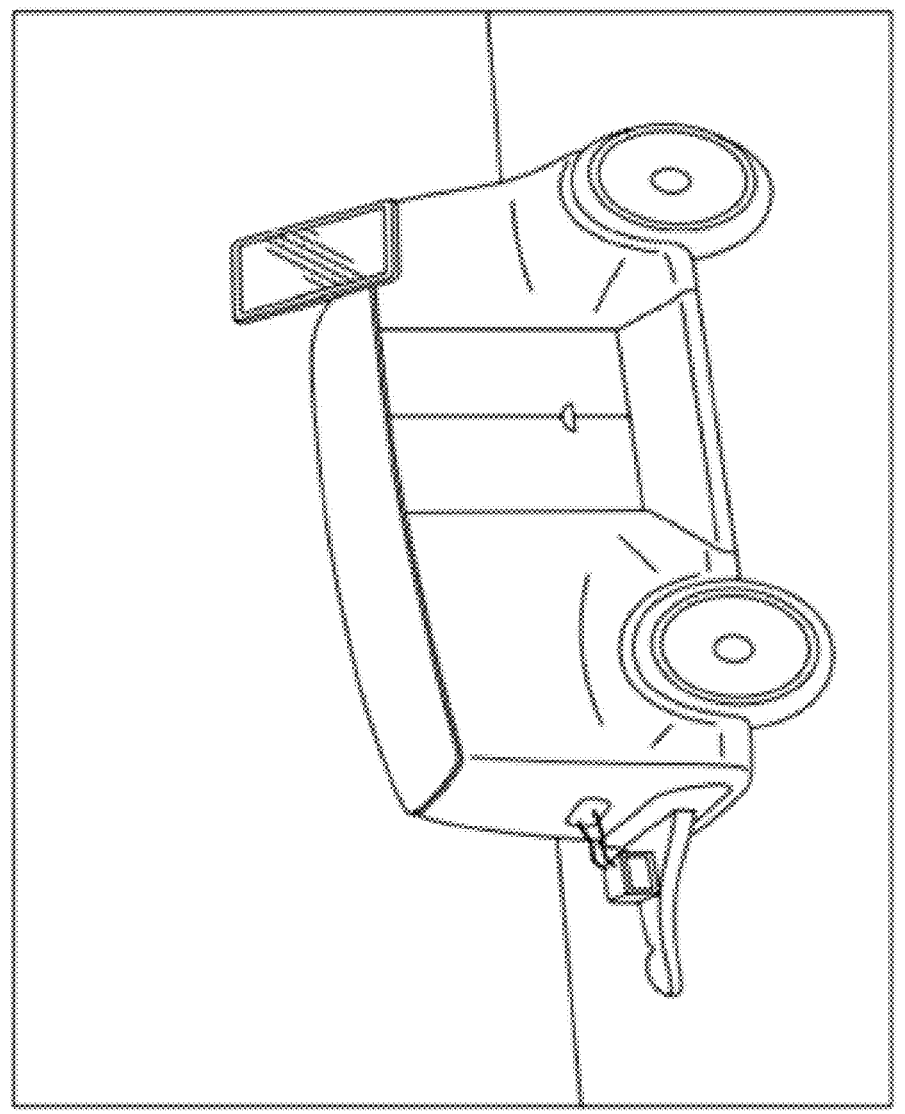
FIG. 4 is a depiction of the apparatus for athletic apparel and turf testing, according to one embodiment of the present invention.
Figure 5:
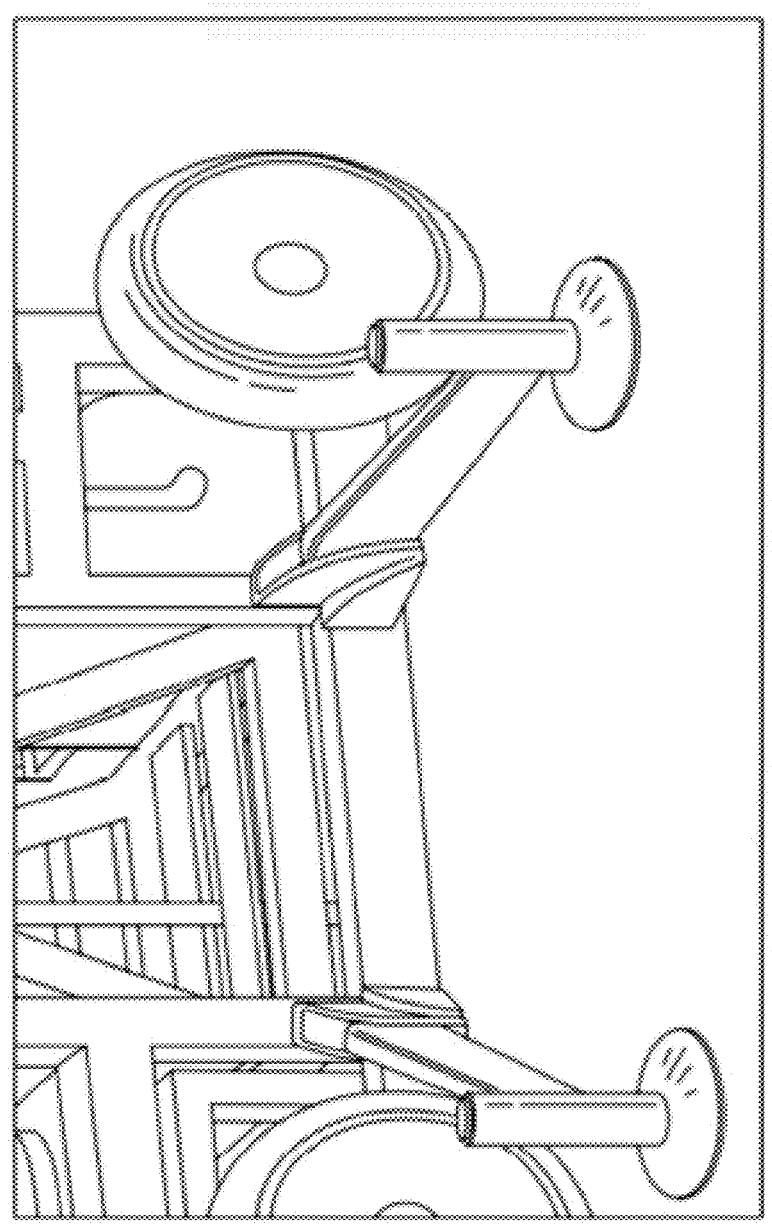
FIG. 5 is a depiction of the apparatus for athletic apparel and turf testing, according to one embodiment of the present invention, including stability fly outs for anchoring the device during testing and/or use.

Turning to the figures, in FIGS. 1-6, and FIGS. 7-9 embodiments are shown comprising certain aspects of the apparatus. In aspects, the apparatus is mobile, wherein the unit may be driven, may be autonomously driven, or may be attached to another vehicle, such as a truck, car, or golf cart (see, e.g., tow hitch attachment or trailer hitch 701, 801, 901). The apparatus may also comprise deployable outriggers, fly outs, or other mechanisms to secure or stabilize the apparatus (711, 811), such as on the turf surface to be tested. (See also, FIG. 5, showing one possible way to secure or stabilize the apparatus during testing.) In aspects, the wheels of the apparatus may be passive, if for example it is towed, but in other embodiments the apparatus may be self-powered in order to be driven by a user or driven autonomously, or by remote control. In embodiments, the apparatus will comprise a data port (706, 806), computer processor, antenna, memory storage unit, receiver, transmitter, controller, battery, charger, charging port, and other electrical components. In aspects, the apparatus may include global positioning systems (GPS) or other devices to, for example, register its position relative to the field or surface being tested. The apparatus may comprise a data acquisition system (DAQ) (709, 809), camera 821, actuator drivers (708, 808), and/or control unit (710, 810). In preferred embodiments, the apparatus will not only test cleat/shoe and surface interaction, but also include sensors to test the field conditions, such as a surface impact hardness sensor 716 and a soil moisture sensor 715, and/or an infill depth probe (712, 812). (See FIGS. 7-9.) Regarding the shoe-surface testing aspects, the apparatus may also comprise a test cleat displacement sensor 823, cleat actuator 822, vertical preload actuator (703, 803), transmission (704, 804), adjustment mechanism (705, 805), a test cleat wrench sensor (713, 813) (such as a multi-axis load cell or multiple single axis load cells), an attachment mechanism (such as a plate), and a test cleat (714, 814) for example on a foot form. In aspects, some of the described elements or all of the described elements may be attached directly or indirectly to the apparatus chassis (702, 802, 707). The apparatus may also comprise an Emergency Power Off (EPO). In aspects, see FIG. 8, the apparatus may include basic cosmetics 817, weatherizing components 818, an operator user interface 819, and process automation 820.

In FIGS. 1 and 4, an embodiment of the apparatus is shown also comprising basic cosmetic components (such as, e.g., material covering the internal mechanisms of the apparatus, like panels or molded plastic), weathering protective elements, an operator user interface, and limited process automation. In other embodiments, the apparatus will comprise a camera or other mechanisms to visually inspect the surface, including turf surface. The apparatus may include the camera attached to the apparatus or employ a drone to hover above the surface for visual inspection. In other aspects, an independent form factor can be a roving drone on wheels.

In further regards to video and computer-implemented visual inspection/analysis of one or more aspects of the turf, including the surface of the turf, which does not necessarily require a foot form or need for interaction of a foot form with the playing surface (e.g., grass or artificial turf), for the purpose of, for example, determining the quality or safety of the turf, aspects of the invention include the following. In embodiments, the invention is a measurement system for repeatably measuring and quantifying turf surface characteristics. Typically, the surface characteristics of artificial turf and natural grass are evaluated and given a rating by an expert in evaluating turf/grass, but the current system can produce repeatable results that can, in aspects, both rate and explain the rating of a surface. In aspects, the system can provide specific/objective results for rating the turf, and do so in a manner that is consistent across different surfaces and across different locations. Accordingly, a result achieved by this system is to extract measurements of turf and natural grass characteristics using a variety of computer vision techniques.

In some cases, such measurements would be difficult or unstable with optical measurement alone. Others would not necessarily be captured accurately using three-dimensional ("3D") scanning. Thus, in aspects, the system can use a single camera, but is not limited to a single camera, to create a combined "optical space" and "depth space" measurement. Additionally, multiple scans can be used for the depth-space image and/or multiple images can be taken with different lighting for optical-space images.

In embodiments, the system can comprise, for example:

a visible spectrum camera, such as an overhead visible spectrum camera, to capture pictures of the turf to be analyzed;

a novel structured light system to take a 3D surface measurement of the turf, with the same camera if possible, although a different or more than one camera are envisioned; and analysis algorithms to extract measurements from the visible spectrum camera and/or the lighting system for taking 3D surface measurements, including self-diagnostic and self-calibration measurements.

In an aspect, more than one laser (e.g., four lasers) orthogonal respective to one another surround a lighting source and camera, such as a light ring and industrial camera. In aspects, the light ring turns on to light the surface and the camera takes the optical image. Then the ring turns off and each laser scans across the surface while being recorded by the same (or a different) camera. Optionally, another optical image is taken after the scan so that the two optical images can be analyzed for differences to account for anything that may have moved during the scan.

In an embodiment, four lasers are used to create four depth maps. The lasers can be mounted facing out and can be bounced off of a spinning mirror into the scan area. Each laser assembly, in aspects, includes a blue laser and a red laser. The blue laser can be chosen automatically if there is too much red in the optical image, which can act to reduces scattering and thereby provide a sharper image on red and orange surfaces. In aspects, stepper motors are used, wherein the stepper motors can have a planetary gear set with a high gearing, such as, by way of example only, 64:1 or 90:1, to offer high and repeatable accuracy once backlash is corrected for. In aspects, the stepper motors can be used to align or aim the mirror(s) to direct the laser(s).

In aspects, any warp of the camera lens is treated/removed using a checkerboard grid. In aspects, then the laser scans are compiled, with the pixels where the laser is seen "tagged" with the depth measurement at that spot. In aspects, the laser scan frames can be stitched together into a depth map by taking the max height for each pixel in the frame during the scan. In aspects, individual lasers contributing to the resulting depth map can be color-coded, and therefore the lasers can fill in each other's shadows and they can see/sense the tips of the fibers.

In aspects, using a single camera, because the scans and the optical images are taken from the same camera, the images can be overlaid, such as exactly or nearly exactly overlaid. In some embodiments, the total entropy in the image is measured, which can assist with quantifying measurement accuracy and/or surface complexity.

If it is desired to measure and understand characteristics of the turf/fiber/grass, the system preferably can accurately separate/delineate the (a) turf/fiber/grass from the (b) infill/dirt. In aspects, it can be easier to make that distinction in the optical image as compared to the depth image. Accordingly, in aspects, the depth image is used to sample the turf/fiber/grass first, but not always. In embodiments, that color sample can be used to find the rest of the fiber in the image and/or scan. According to this process, a mask is created, sometimes referred to as the fiber mask, which is an important component output of the system, because it can allow a user to determine more information/measurements about the turf/fiber/grass and infill/dirt individually and/or separately.

Using the fiber mask to isolate the two components of the surfaces, the system can now expand the measurements to a host of new measurements, such as:

For Turf:

Distribution of total height from ground and/or height of exposed fiber over infill;

Variation of detected heights (coverage/density);

Distribution of categories represented in the visible image (coverage/evenness/patchiness); patches of exposed infill;

Tape width/wear using blob detection or filtered line detection (fiber quality/splitting); and/or The "lay" of the turf, which can be determined by, for example, the orientation of detected blobs and the perpendicular direction to height gradient.

For Natural Grass:

Color distribution of grass(es); detection of grass color, paint, and potentially other artifacts; early onset diseases and pests; toxicity to chemical inputs; and physiological and morphological changes such as seedhead development, etiolation, and other adaptations to abiotic stresses;

Distribution clusters of color in the visible image, developing species/seasonality benchmarks (coverage/evenness); and/or Distribution of categories represented in the visible image (coverage/evenness/patchiness); patches of exposed dirt.

In aspects, the system determines features of the grass/turf/fibers/in-fill that can be reliably extracted, and several different ways of presenting each feature are presented to a user (e.g., a single metric, a distribution, distributions over time, and others) so that the user can understood, troubleshot, and integrate partial data into the rest of the data from the system.

Calibration Routine

In aspects, in order to ensure that the depth measurements are accurate using the system, a "calibration square" is scanned as part of a one-off calibration routine for machine setup. If the shape or form-factor of the machine changes, this calibration can be redone. Otherwise, one calibration can, in aspects, be useful for the life of the machine. In aspects, the calibration square can be a 150 mm×150 mm square with a 25 mm lip on an edge. It can be used as a known reference target and to deduce laser position and depth.

An example of the Calibration Routine is as follows: first a calibration square is place into a calibration frame, which positions the square in the center of the frame and orthogonal to the one or more lasers. In cases, one or more corners of the square is located/determined and the image is warped so that the square fills the frame. This can ensure that the scans are orthogonal to the frame an in alignment with the one or more lasers. Once the square is isolated, known aspects of the dimensions of the square can be used to measure what is being seen/sensed across the scan, extracting laser position and step from each frame. A line can then fit to each of the two in order to create a map of where the laser is over time in a scan; in other words, the position of the laser over time, in aspects, will form a line, which can be fit in order to model the laser position over the time of the scan, which can allow for deduction of depth by measuring how far the laser diverges from that predicted position. These line-of-best-fit equations can be saved in a calibration file and can be used to model where lasers are in the frame over time for future scans.

Software Architecture Features

In embodiments, the menu user interface can allow a user to run scans, recalibrate the system, run analysis separately from scans, and run tests. It can, in aspects, also automatically update the code and the controller on start-up. Features include, but are not limited to:

Camera adapter—works with cameras in an async loop to start and end recordings;

Controller adapters—works with control systems to operate custom machinery;

Storage adapters—stores data in cloud storage as well as the local file system as a backup, for example, although data can be stored on the system, on the system device, on an electronic device, and/or on a remote electronic device;

Alert adapters—receive alerts, such as on Slack™ or Zapier™, by way of example;

Location adapters—flexible and extensible location handling;

Records system—for organizing data on studies and the locations within them;

Analysis system—for extracting data from single frames, scan locations, and full studies; and/or Controller code—main microcontroller control logic plus other diagnostic scripts.

Example

The following is by way of example only and is not limiting to the scope of the present invention described herein.

Menu System

Main menu items include functionality such as the following, by way of example only:

Check system ready—check to see if the machine camera and controller are connected and working.

Run scan loop—wait for presses on the button on the machine to scan. Delay analysis until the end.

Run single scan—run a single scan and analyze immediately.

Start a single scan and skip analysis—just collect the data.

Home all lasers—run the homing routine on the machine to align the mirrors. Will also run before other operations.

Clear shell—clear old data from the console.

Figure 7:
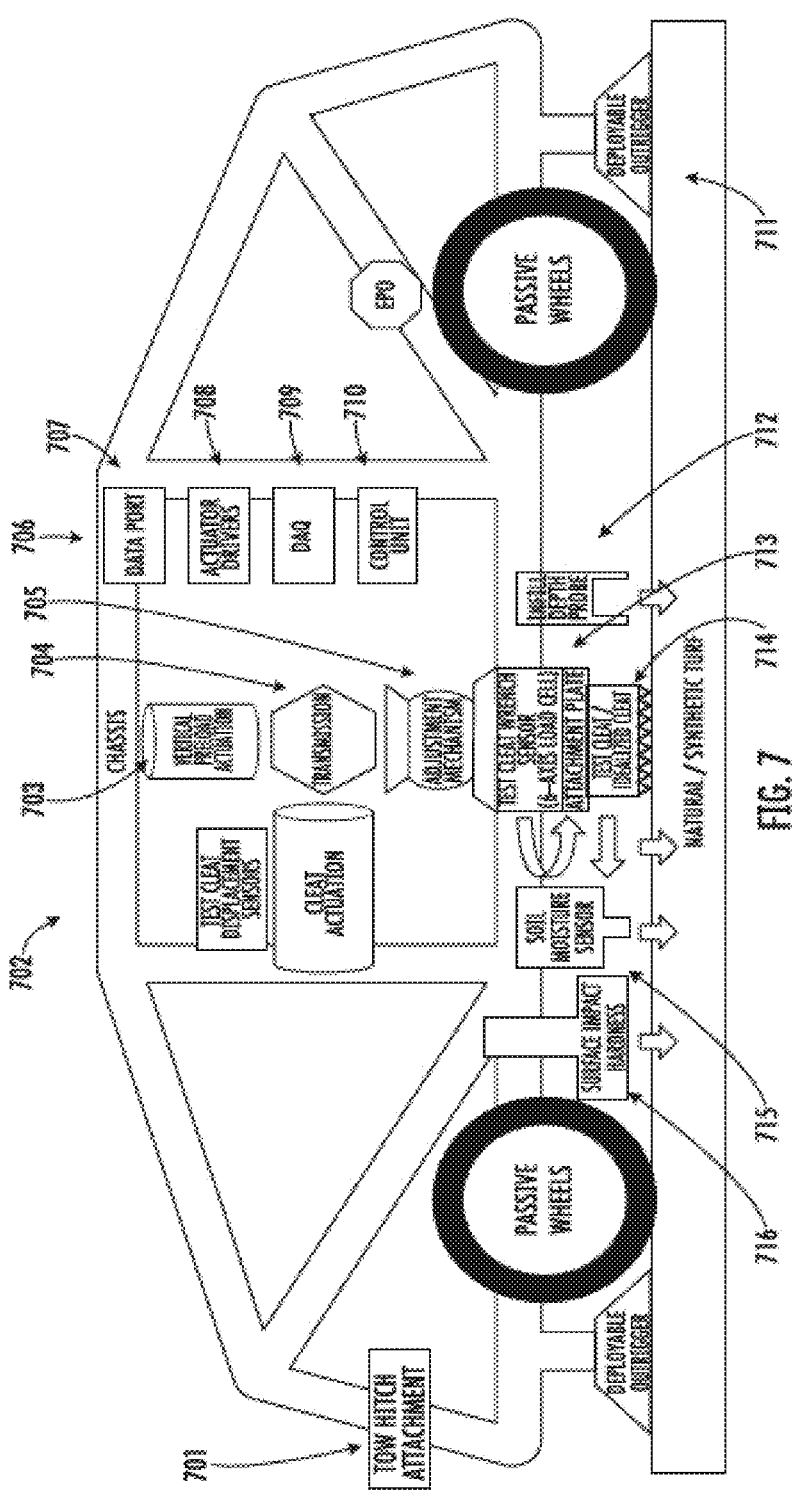
FIG. 7 is a depiction of the apparatus for athletic apparel and turf testing, including labeled aspects comprising parts of the apparatus, according to one embodiment of the present invention.
Figure 8:
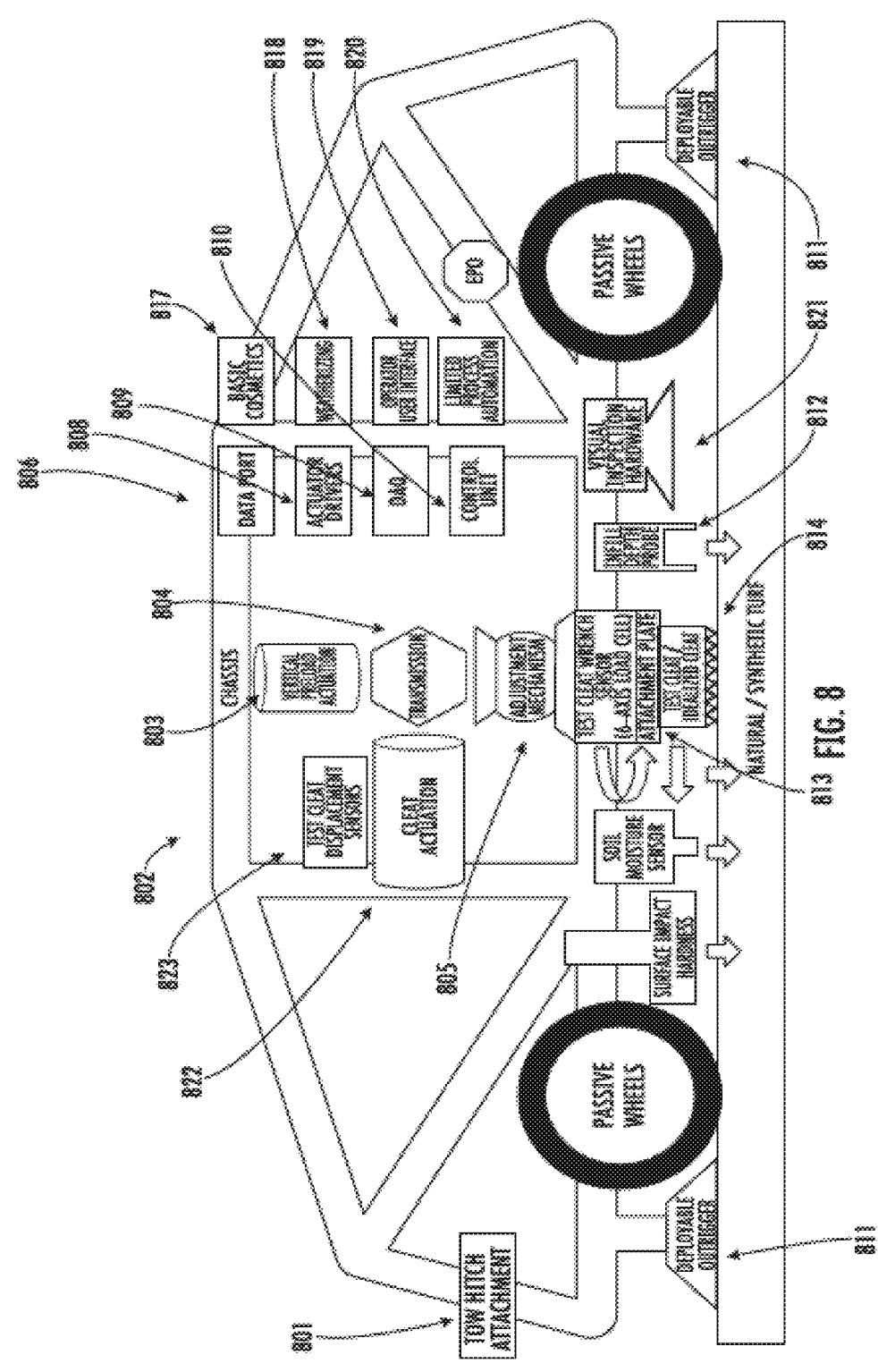
FIG. 8 is a depiction of the apparatus for athletic apparel and turf testing, including labeled aspects comprising parts of the apparatus, according to one embodiment of the present invention.
Figure 9:
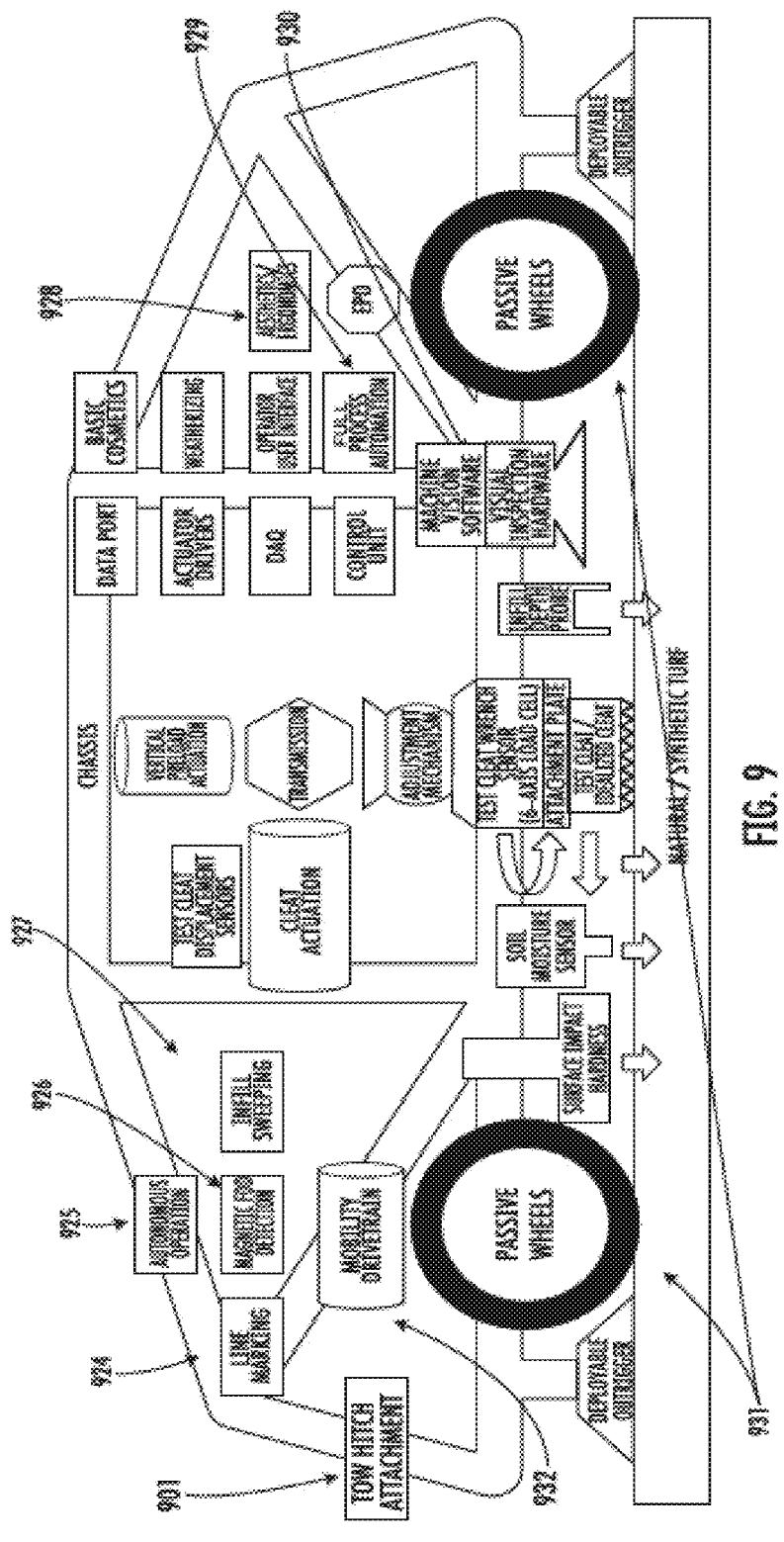
FIG. 9 is a depiction of the apparatus for athletic apparel and turf testing, including labeled aspects comprising parts of the apparatus, according to one embodiment of the present invention.

For system architectural embodiments, shown in FIGS. 7-9, the apparatus may comprise additional elements, including but not limited to the capability to mark lines on the turf 924 (such as hash marks), user interface aesthetics and ergonomics 928, full process automation 929, a mechanism for autonomous operation 925, magnetic foreign object debris (FOD) detection 926, and the capability to infill sweep 927. In the embodiment shown in FIG. 9, for example, the apparatus is shown wherein it can be driven, including driven wheels 931 and a mobility drivetrain 932. This embodiment also shows where the camera or other visual inspection mechanism use machine vision technology/hardware and software 930.

In further aspects of the invention, the apparatus can be configured to include some or all of the mentioned elements such as line marking, magnetic FOD detection, infill sweeping, testing infill for bacteria agents, automatic data uploading to server, automated all user processes, fully autonomous system, and/or drone assist full field inspection from above.

Figure 23:
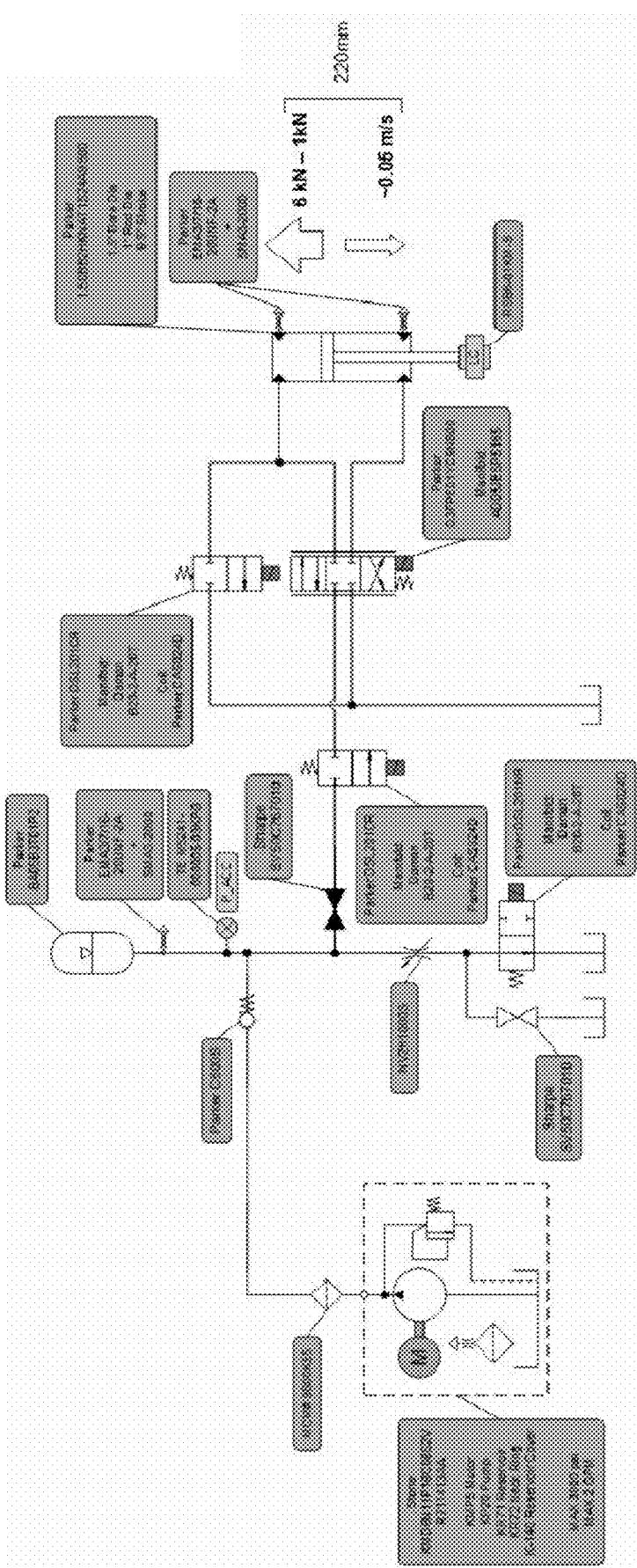
FIG. 23 is a diagram of the device power architecture according to one embodiment of the present invention.

As shown in FIGS. 10 and 23, by way of example, the target power numbers may include up to a 8 kN preload, a horizontal (longitudinal or lateral or oblique) force range up to 10 kN, and a torque range up to 400 Nm. Displacement may include up to 500 mm translation and/or up to 225 degrees rotation. Instantaneous power requirements may be accomplished via a multi-actuator driven system. In other aspects, a hydraulic Stewart platform may be used. Due to the design of the current invention, it allows for higher forces to be applied, including up to providing 400 Newton-meters of torque; up to 8,000 Newtons of vertical force; and up to 10,000 Newtons of horizontal force; individually or at the same time. In a particular embodiment, by way of example, vertical preload may be from 0.10-6.0 kN, translation pull force may be up to 10 kN, rotational torque may be up to 400 Nm, translation speed may be around 3.5 m/s, rotation speed may be around 2500 deg/sec [43.6 rad/s], and cleat-turf interface adjustability is possible in the roll, pitch, and yaw orientations/directions. The invention may also limit compliance of the footform in unconstrained degrees of freedom during the shoe-surface interaction, so that test conditions are maintained as accurately as possible. The invention is intended to operate in temperatures ranging from, but not limited to, 0-100 degrees Fahrenheit. In one embodiment of the invention, the size of the invention may be approximately 7.0 feet long by 4.0 feet wide by 4.0 feet high, while the weight may be between 1,000-3,000 lbs.

Figure 2:
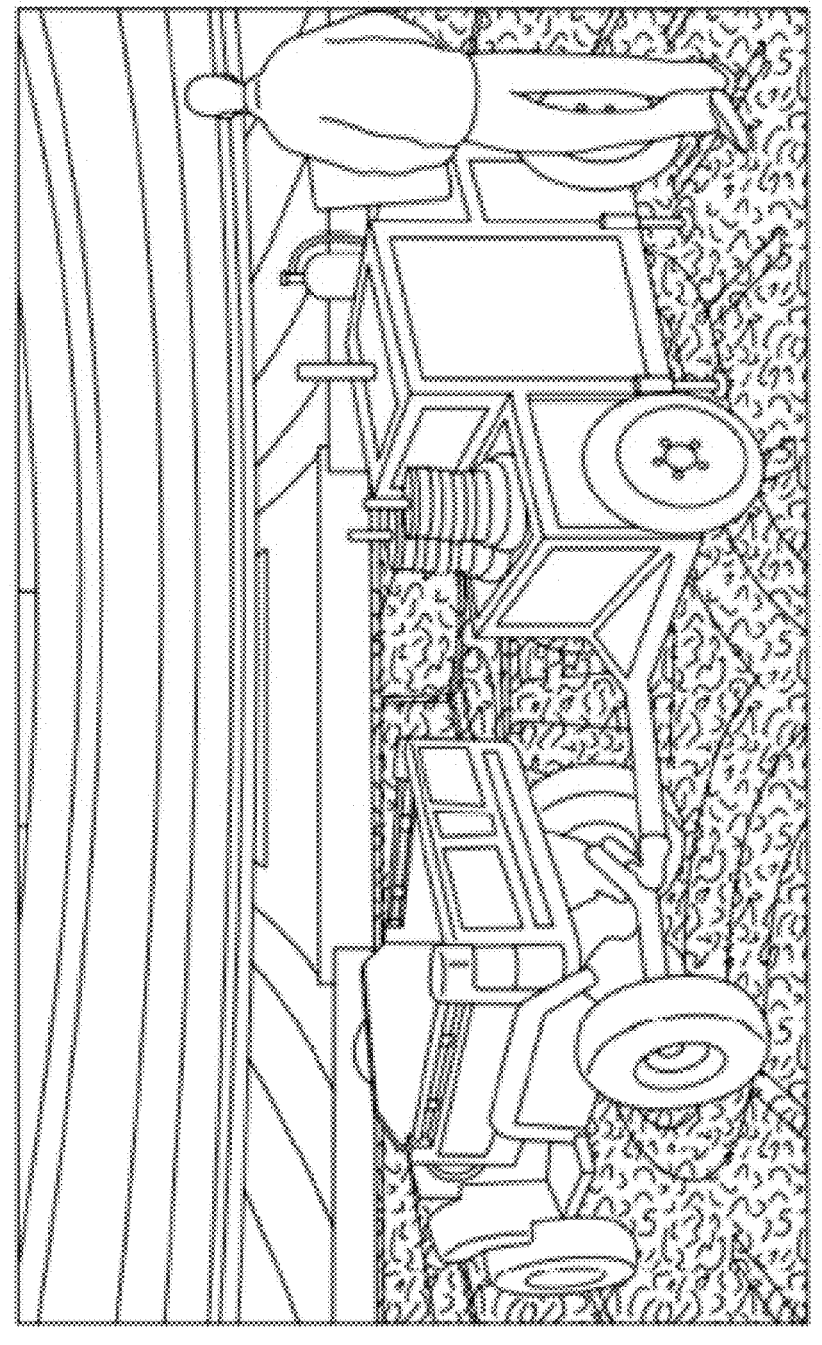
FIG. 2 is a depiction of the apparatus for athletic apparel and turf testing, according to one embodiment of the present invention.
Figure 11:
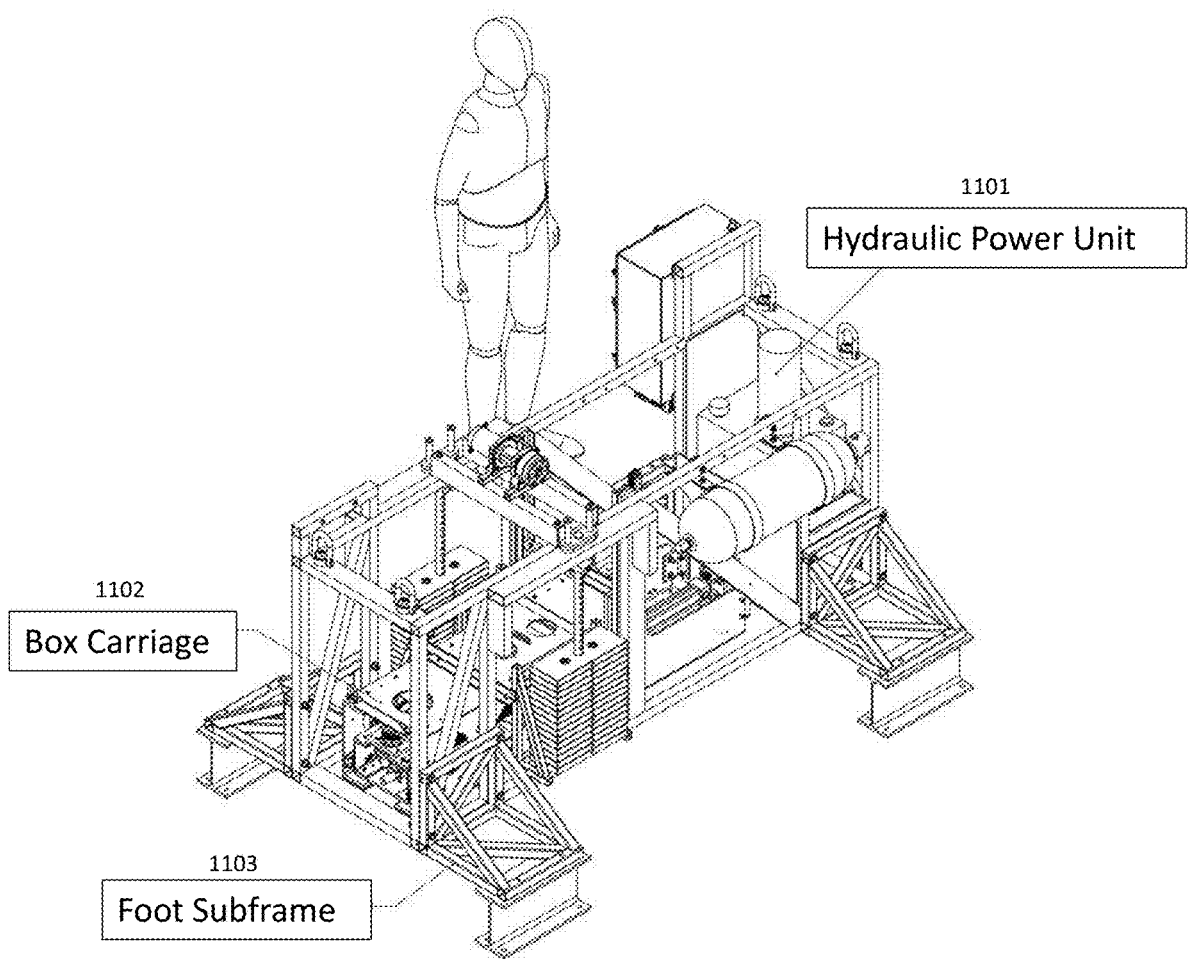
FIG. 11 is a depiction of the apparatus for athletic apparel and turf testing, including labeled aspects comprising parts of the apparatus, according to one embodiment of the present invention.
Figure 12:
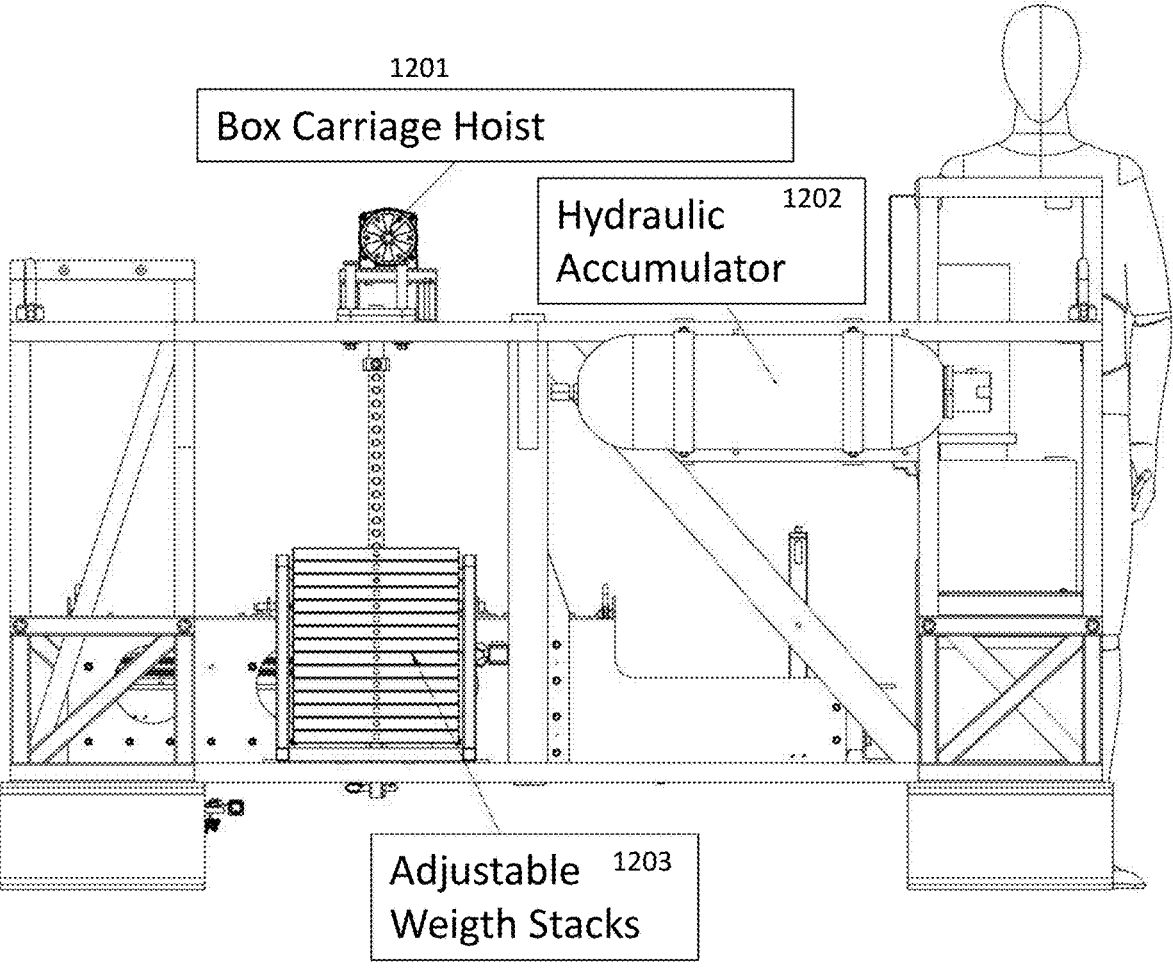
FIG. 12 is a depiction of the apparatus for athletic apparel and turf testing, including labeled aspects comprising parts of the apparatus, according to one embodiment of the present invention.
Figure 13:
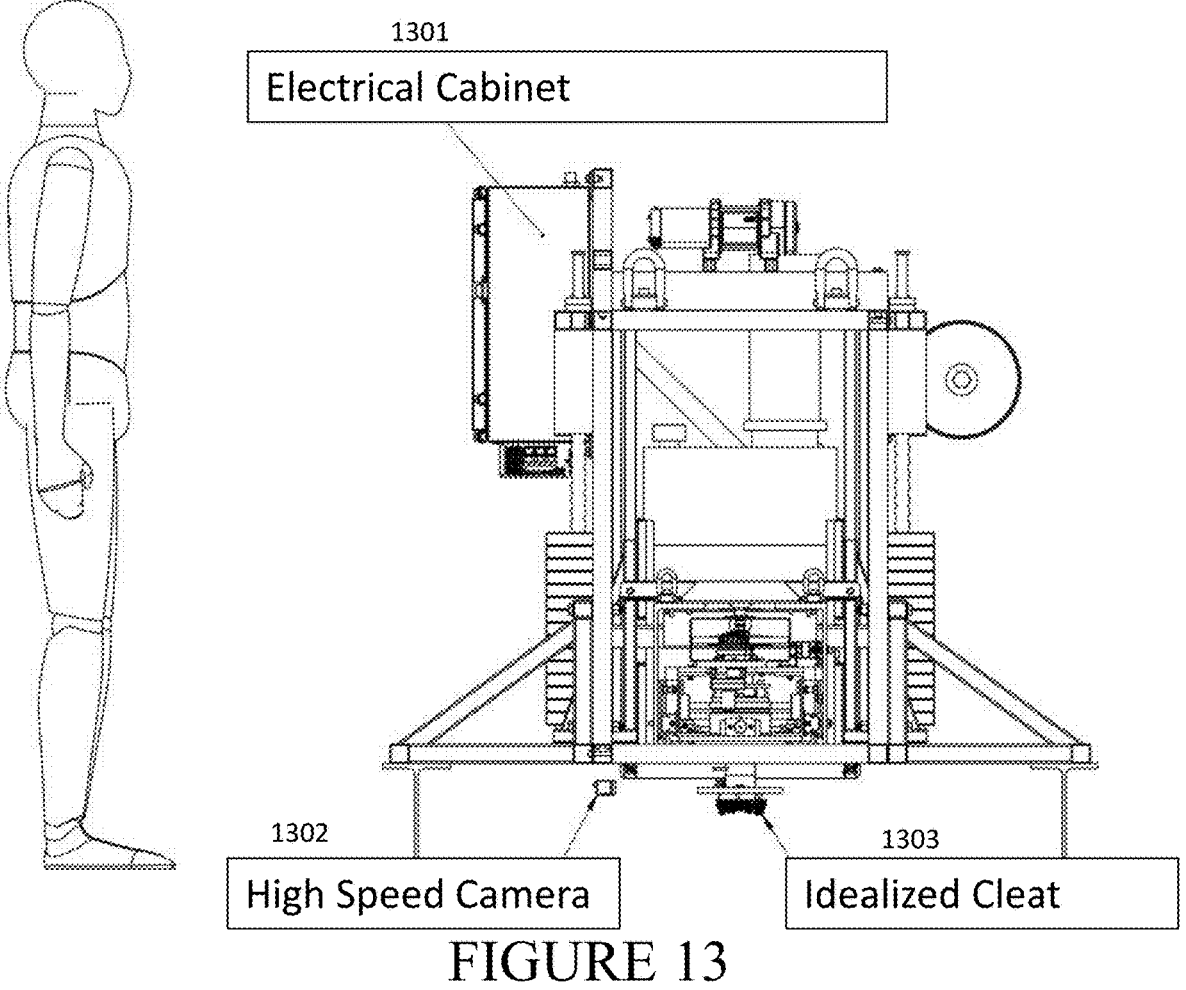
FIG. 13 is a depiction of the apparatus for athletic apparel and turf testing, including labeled aspects comprising parts of the apparatus, according to one embodiment of the present invention.
Figure 14:
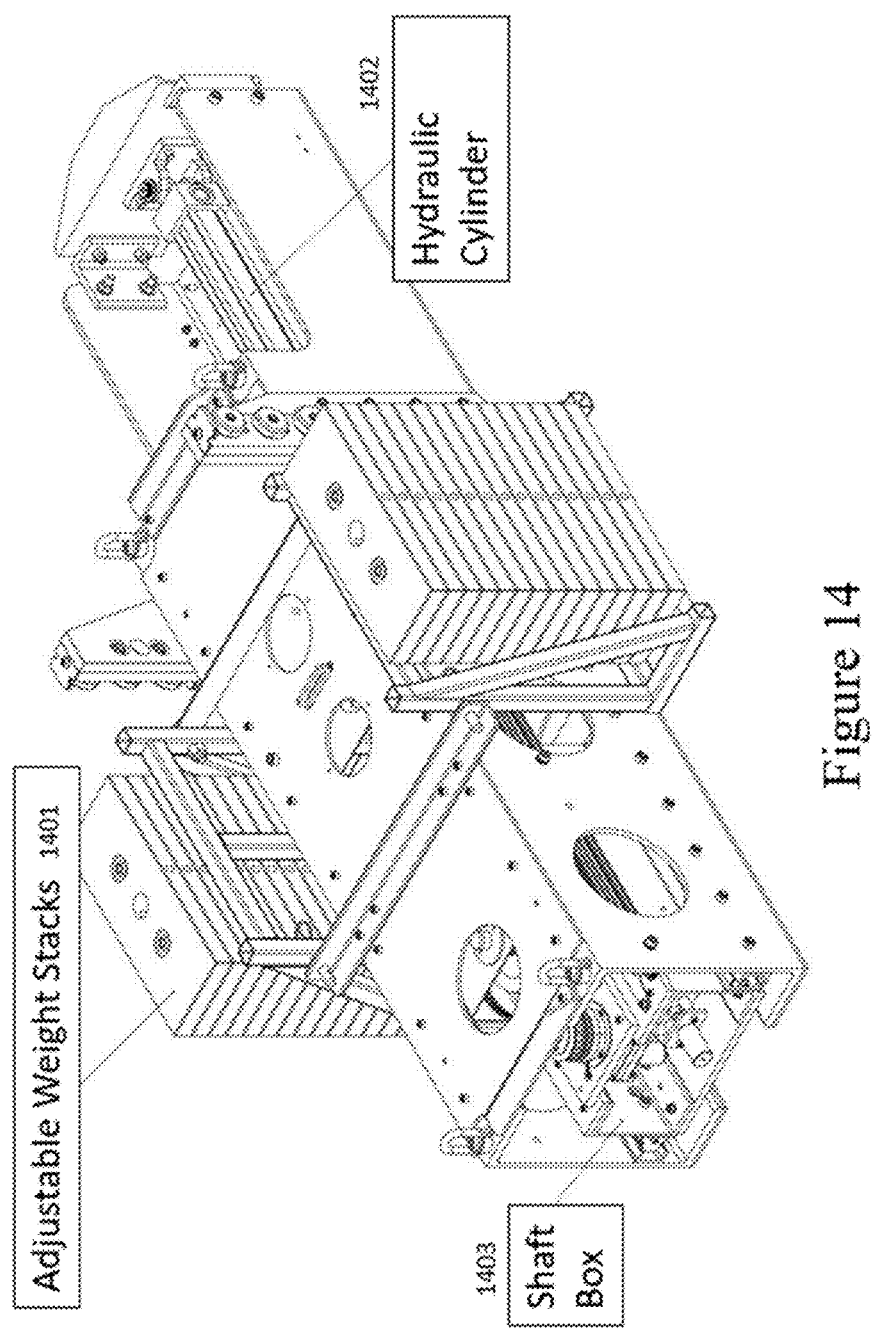
FIG. 14 is a depiction of the apparatus for athletic apparel and turf testing, including labeled aspects comprising parts of the apparatus, according to one embodiment of the present invention.
Figure 15:
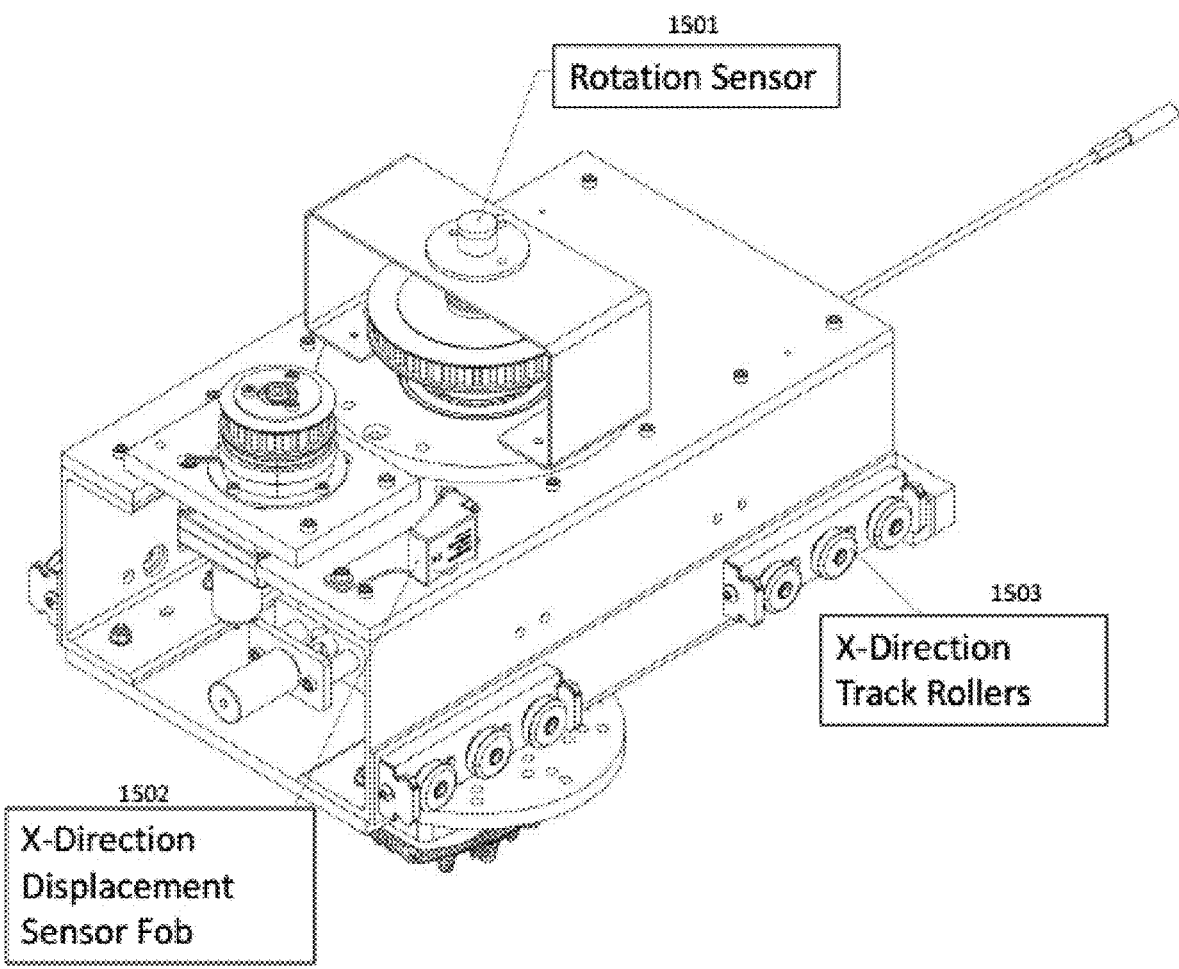
FIG. 15 is a depiction of the apparatus for athletic apparel and turf testing, including labeled aspects comprising parts of the apparatus, according to one embodiment of the present invention.
Figure 16:
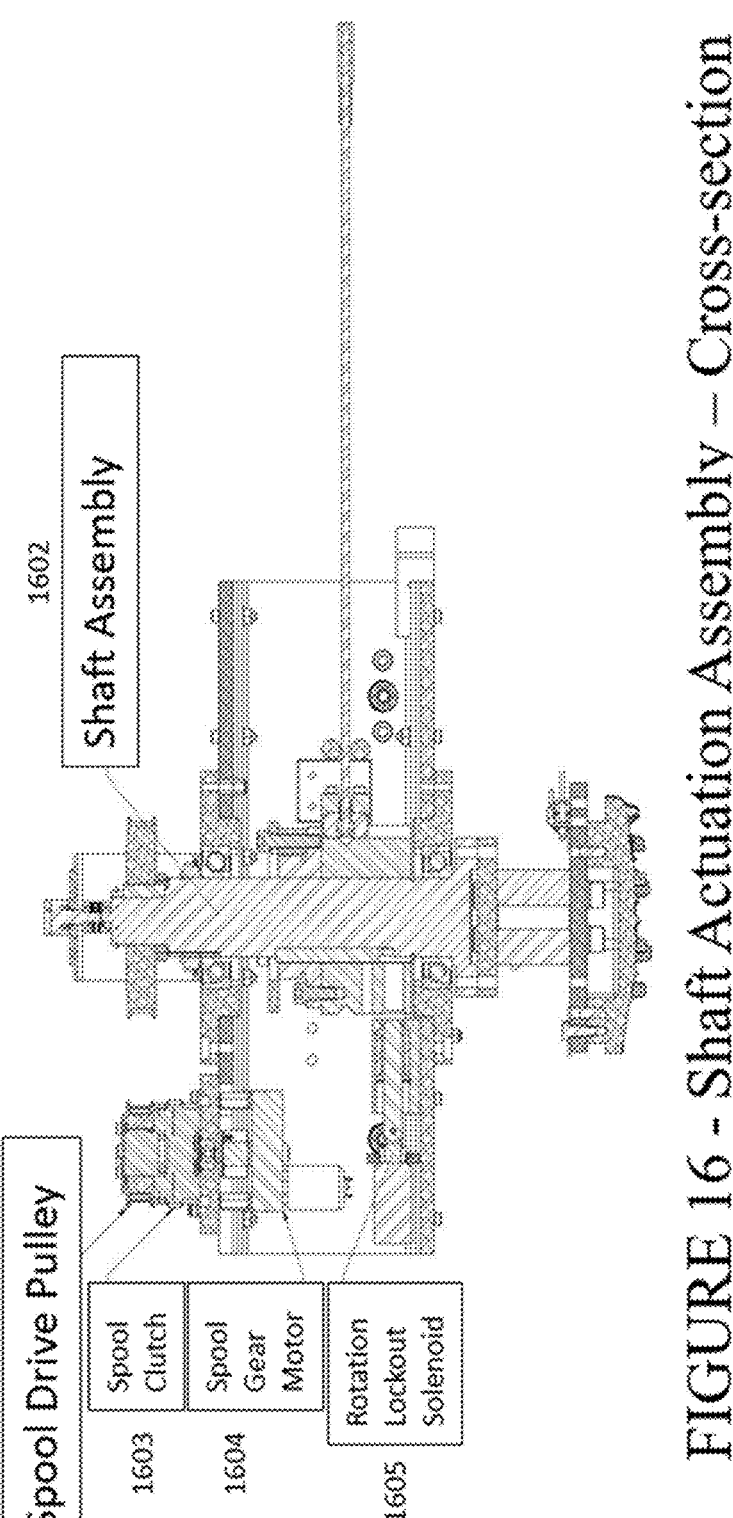
FIG. 16 is a depiction of the apparatus for athletic apparel and turf testing, including labeled aspects comprising parts of the apparatus, according to one embodiment of the present invention.
Figure 17:
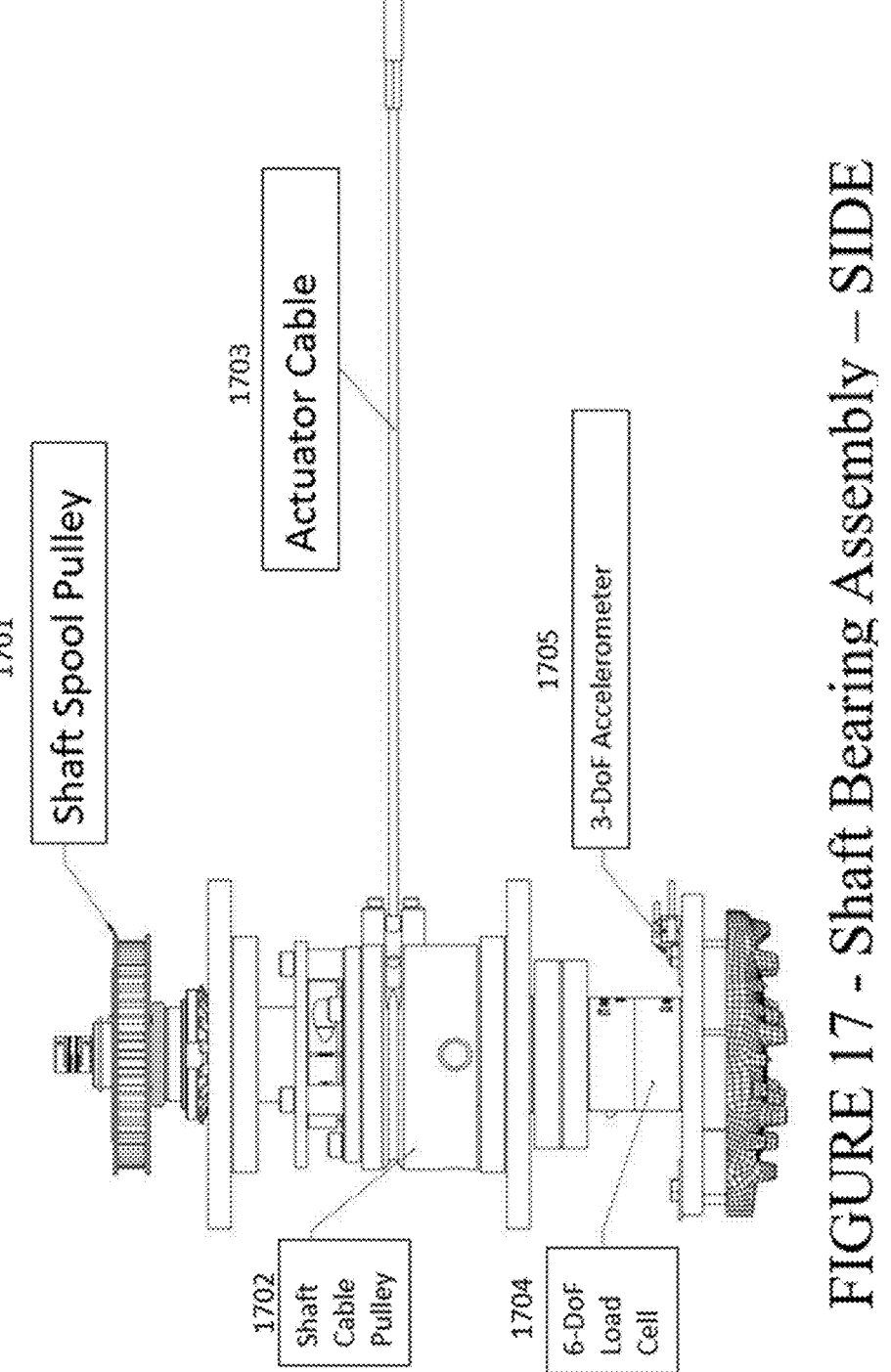
FIG. 17 is a depiction of the apparatus for athletic apparel and turf testing, including labeled aspects comprising parts of the apparatus, according to one embodiment of the present invention.
Figure 18:
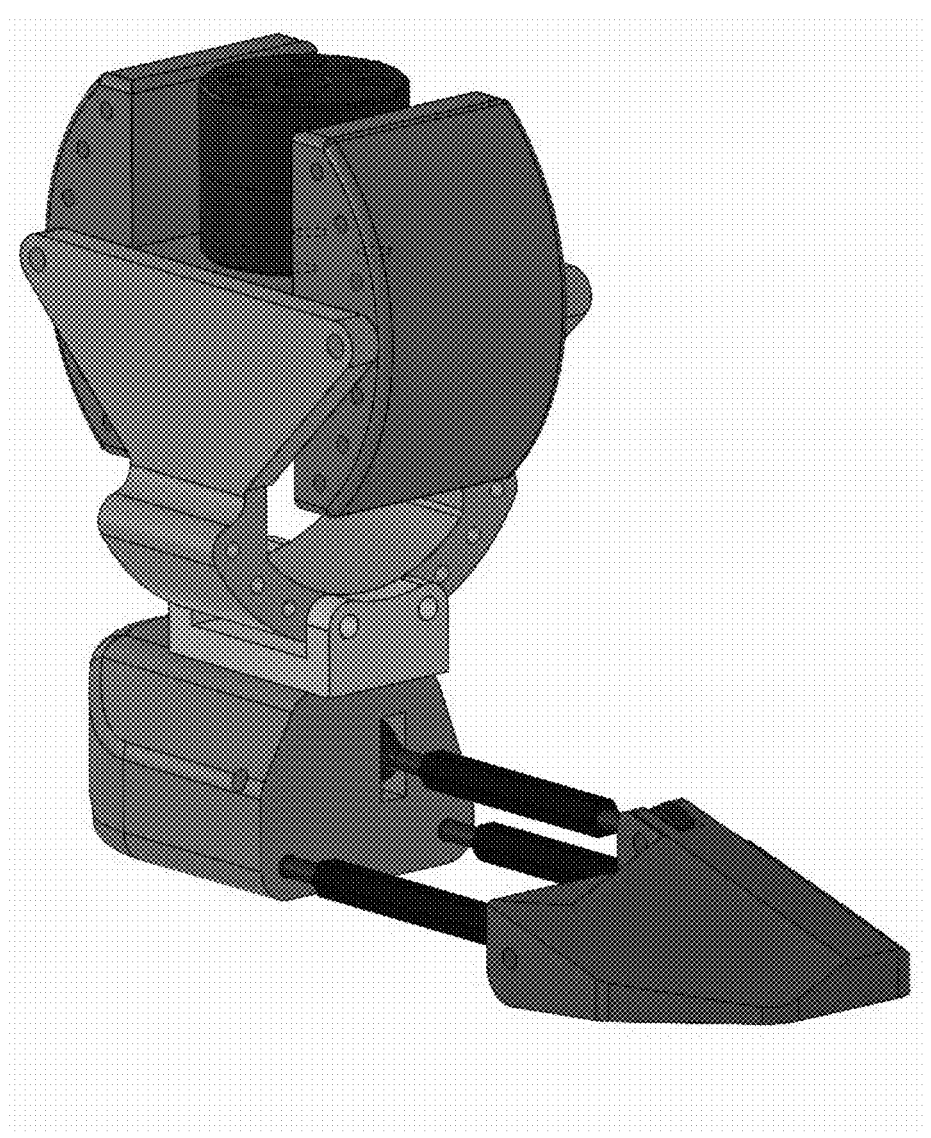
FIG. 18 is a depiction of an aspects of the apparatus for athletic apparel and turf testing, according to one embodiment of the present invention.
Figure 20A:
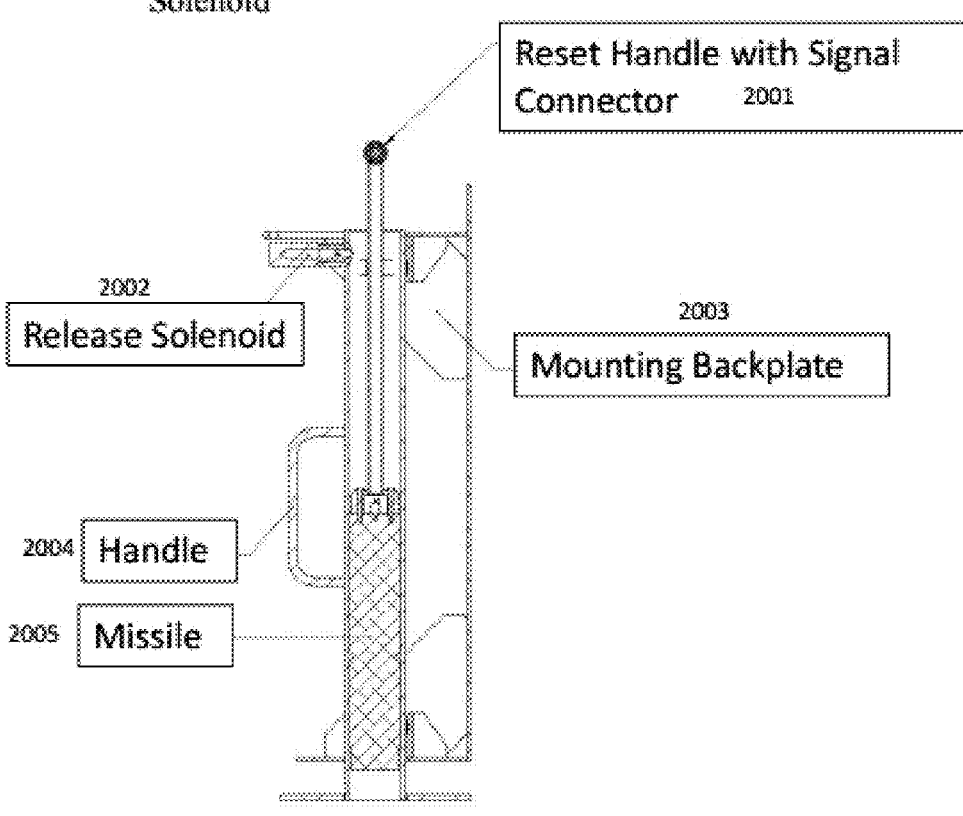
FIG. 20A is a depiction of the apparatus for athletic apparel and turf testing, including labeled aspects comprising parts of the apparatus, according to one embodiment of the present invention.
Figure 20B:
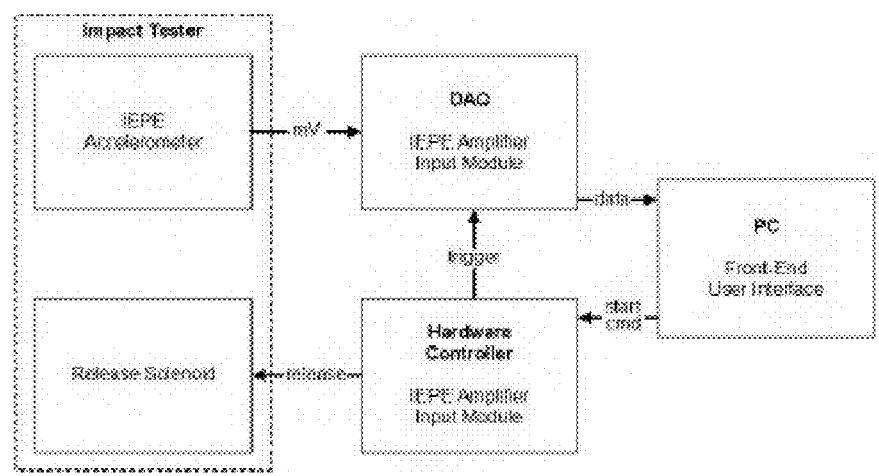
FIG. 20B is a diagram of an integration data collection logic loop according to an embodiment of the present invention.
Figure 21:
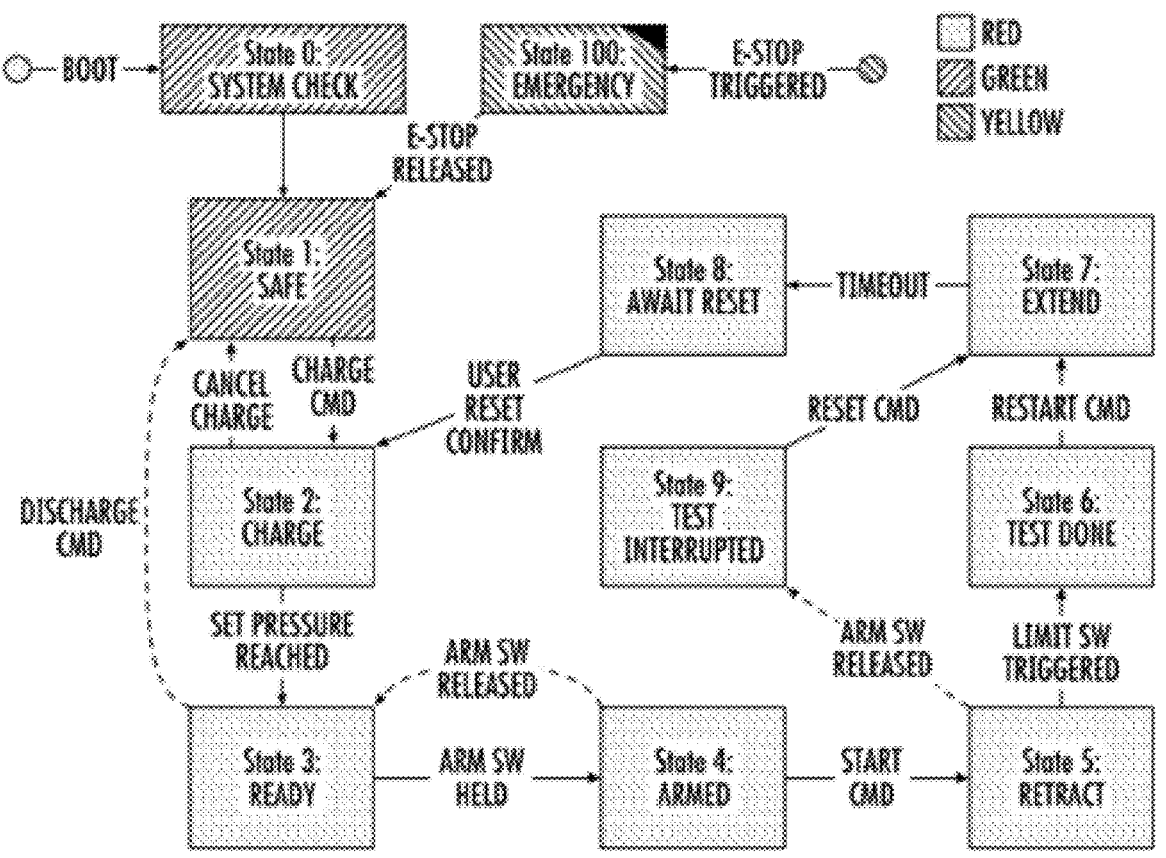
FIG. 21 is a depiction of the actuation architecture according to one embodiment of the present invention.
Figure 22:
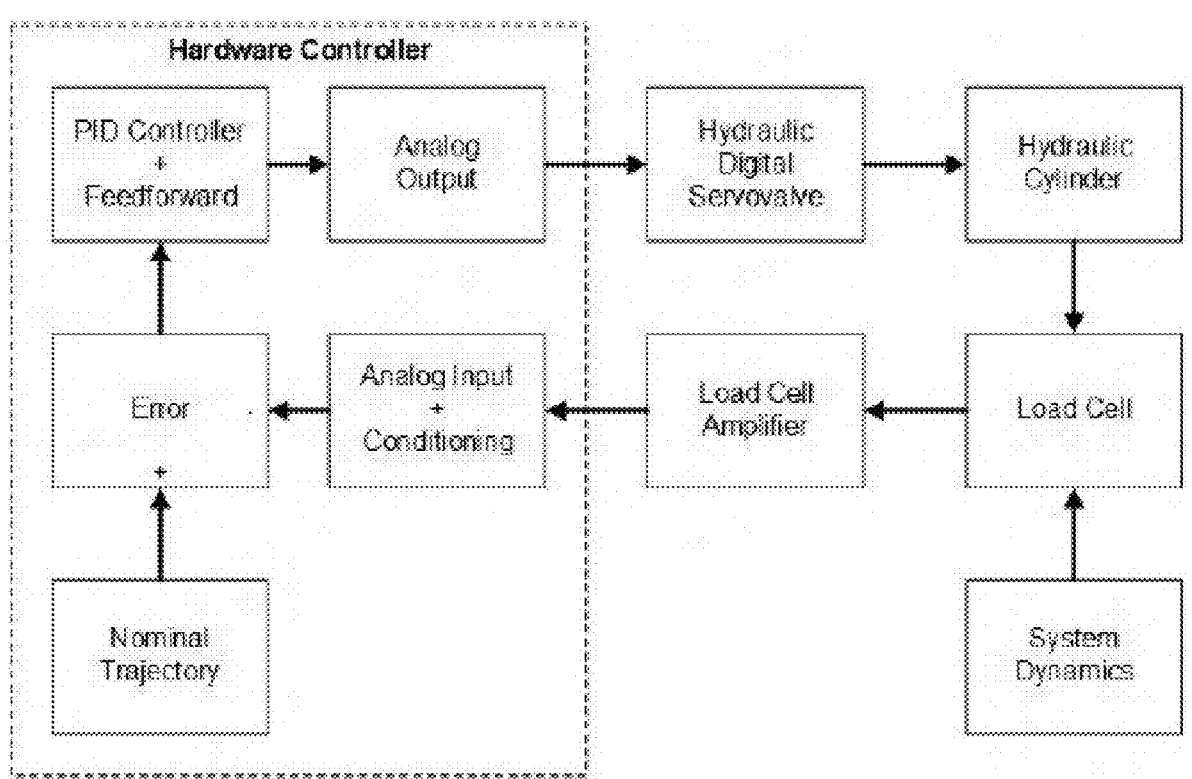
FIG. 22 is a flowchart of the device control according to one embodiment of the present invention.

Design schematics comprise several other Figures. FIG. 1 shows an embodiment of the invention including aesthetic paneling and molded material covering the internal structure of the apparatus. In this particular embodiment, the apparatus may be driven manually or autonomously, or by remote control. In FIG. 2 and FIG. 3, an embodiment is shown of the apparatus wherein it is passive and towed by another vehicle, with and without exterior body panels. Similarly, in FIGS. 5 and 6, the apparatus is shown with add-ons that extend capability by increasing stability and with touch-screen human-machine interface, respectively. FIGS. 7-9 show embodiments of system architecture of the core device (see, e.g., FIG. 7), as well as with add-on systems that extend capability, such as computer vision (see, e.g., FIG. 8), and self-propulsion (see, e.g., FIG. 9). FIG. 10 is an example of hardware available for test actuation in the load and rate regimes to replicate athlete cleat-turf interactions. FIGS. 11-13 show embodiments of design schematics for the full device in isometric, side, and front reliefs, respectively. A notional human is provided for scale. Specifically, FIG. 11 shows the apparatus including a box carriage 1102, hydraulic power unit 1101, and foot subframe 1103. FIG. 12 shows the apparatus including a box carriage hoist 1201, a hydraulic accumulator 1202, and an adjustable weight stack 1203. FIG. 13 shows the apparatus including an electrical cabinet 1301, a high-speed camera 1302, and an idealized cleat 1303. FIGS. 14-17 show design schematics for embodiments of the mechanical subsystems governing the mechanism translation (see FIG. 14) and rotation (see FIGS. 15-17). Specifically, FIG. 14 shows a subsystem including adjustable weight stacks 1401, hydraulic cylinder 1402, and a shaft box 1403. FIG. 15 shows a subsystem including a rotation sensor 1501, an x-direction displacement sensor fob 1502, and x-direction track rollers 1503. FIG. 16 shows a subsystem including a spool drive pulley 1601, a shaft assembly 1602, a spool clutch 1603, a spool gear motor 1604, and a rotation lockout solenoid 1605. FIG. 17 shows a subsystem including a shaft spool pulley 1701, a shaft cable pulley 1702, an actuator cable 1703, a 6-DoF load cell 1704, and a 3-DoF accelerometer 1705. FIG. 18 is a design schematic of an embodiment of the surrogate footform, capable of articulating at the 'ankle' and 'toe' joints, in this example, whilst being shod in standard footwear. FIG. 19 is a design schematic of an embodiment of the turf datum finder for establishing a reference height of the turf relative to the rest of the device actuation assembly, including a non-contact limit switch 1901, a cage with mounting flange 1902, and a probe stem 1903. FIG. 20A shows a design schematic of an embodiment of the impact test device, including a reset handle with signal connection 2001, a release solenoid 2002, a mounting backplate 2003, a handle 2004, and a missile 2005, and FIG. 20B shows its integration data collection logic loop. FIG. 21 is a diagram outlining an embodiment of the actuator and power states of the device during different set points in the acquisition process. FIG. 22 shows and automatic control logic diagram for an embodiment of the device, allowing for the use of real-time or near-real-time computer-mediated adjustments to the device actuation in response to the loads/moments perceived at the cleat-turf interface. FIG. 23 is a power flow diagram outlining an embodiment of how the electrical and pneumatic power systems communicate across the device to actuate the device mechanism.

Figure 6:
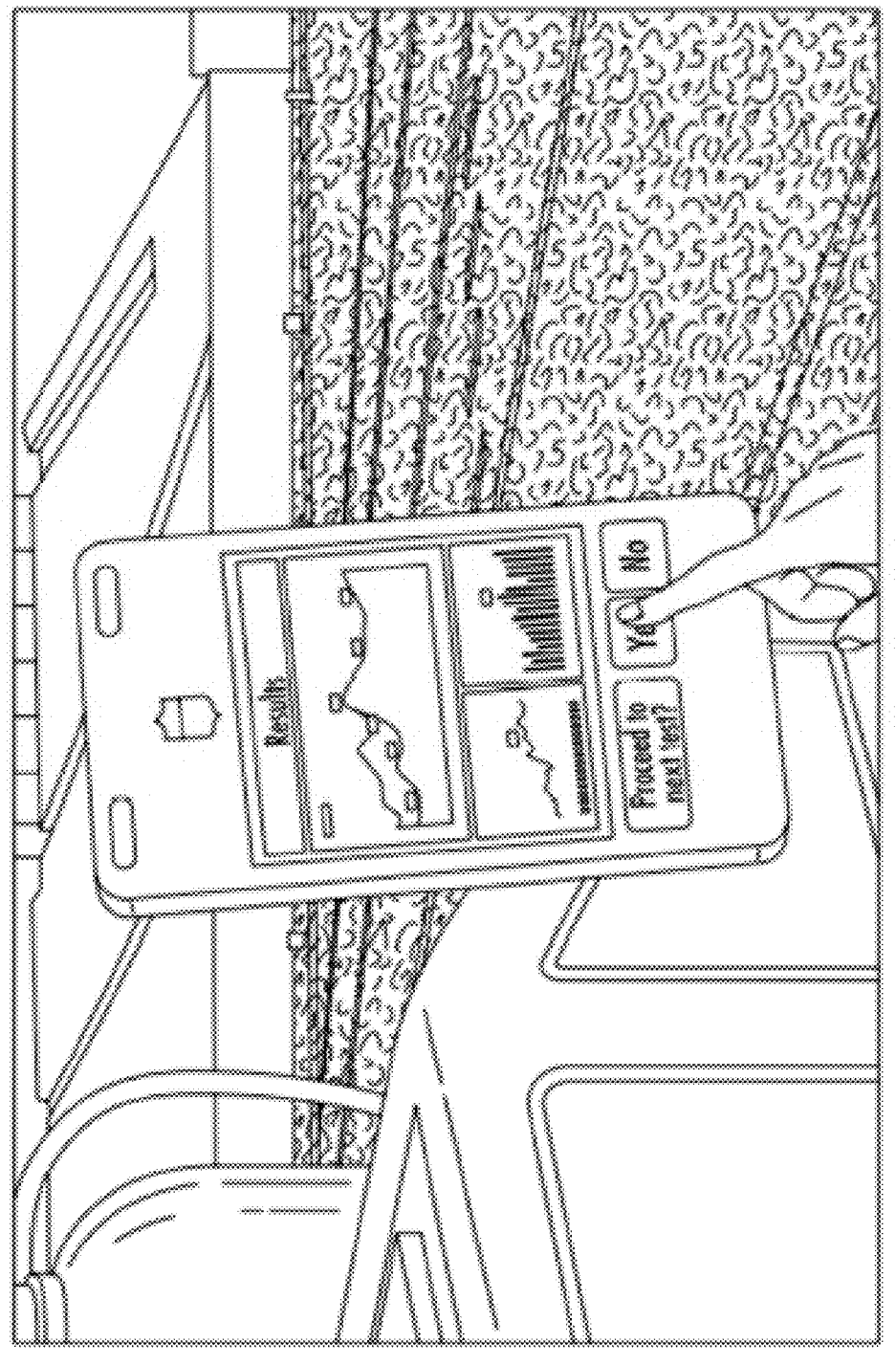
FIG. 6 is a depiction showing using the apparatus via a touchscreen computer module (e.g., a tablet computer or mobile phone), according to one embodiment of the present invention.

FIG. 6 shows that a tablet computer, mobile phone, or other portable electronic device may be used to control the apparatus and/or review the test data, by way of example only. Embodiments of the invention include a computer readable medium comprising one or more computer files comprising a set of computer-executable instructions for performing one or more of the calculations, steps, processes and operations described and/or depicted herein. In exemplary embodiments, the files may be stored contiguously or non-contiguously on the computer-readable medium. In aspects, the files or data may be sent directly or indirectly to the cloud or remote servers(s). Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

Figure 24:
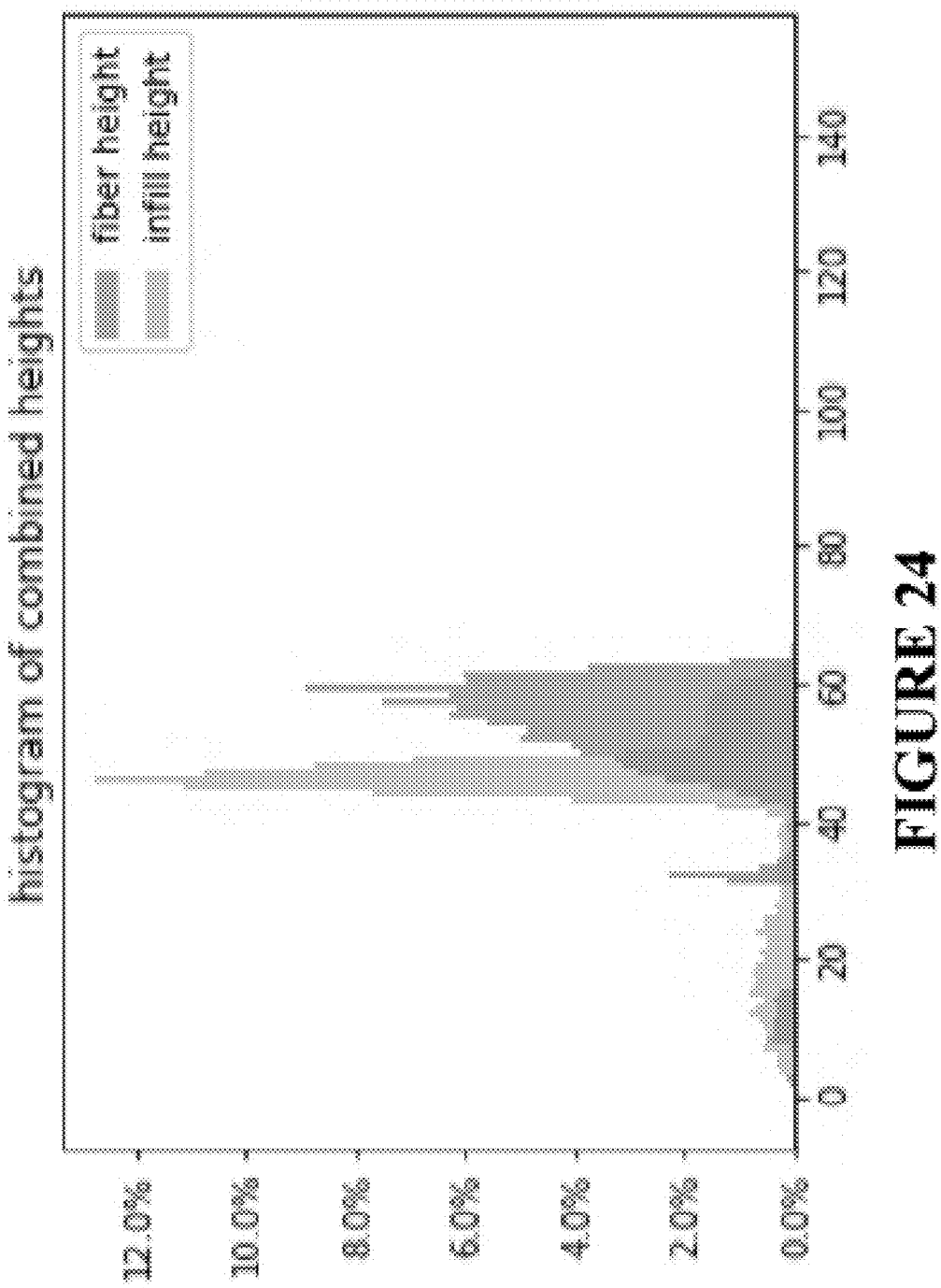
FIG. 24 is a graph showing histogram of combined heights according to aspects of the current invention.
Figure 25:
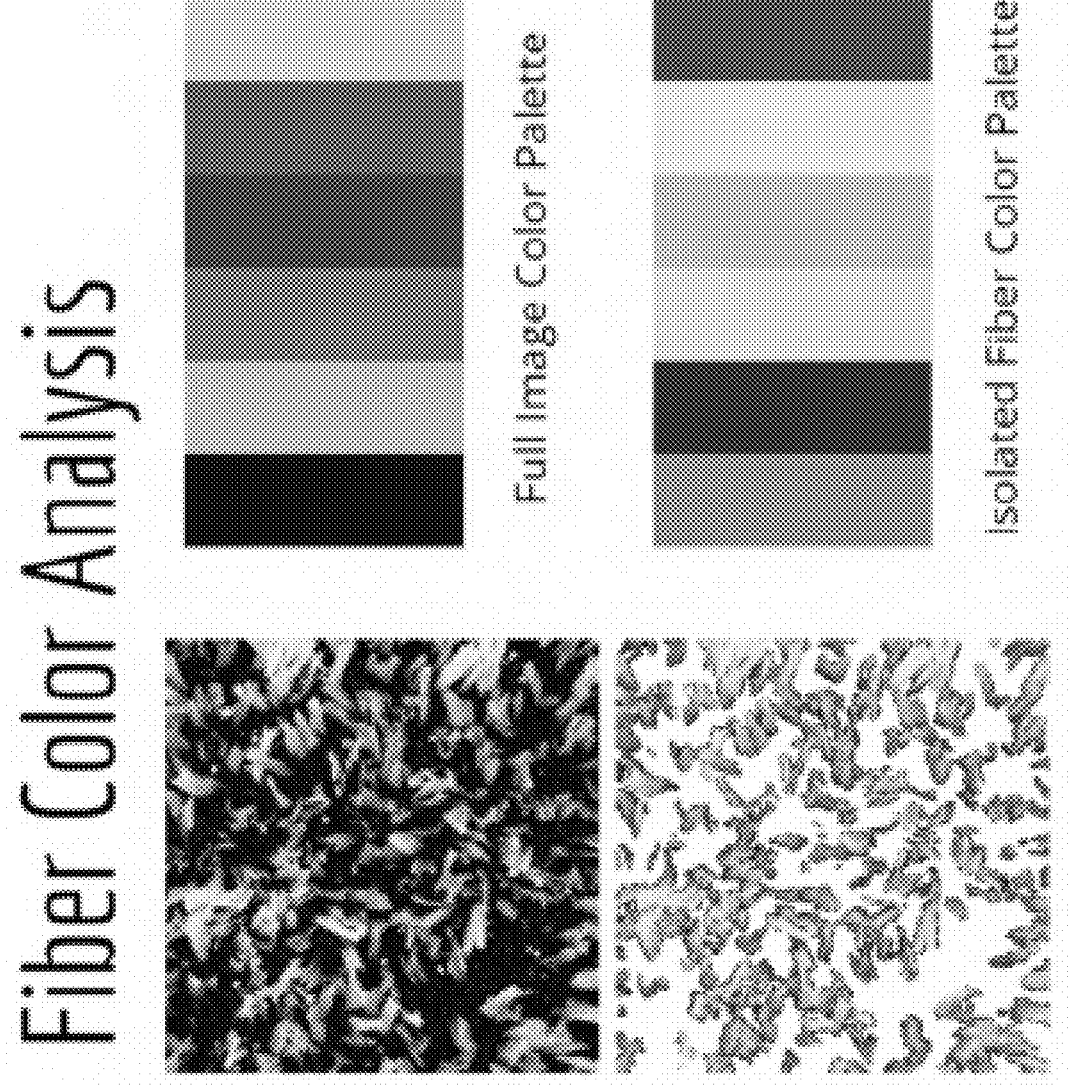
FIG. 25 is a depiction showing a fiber color analysis according to aspects of the current invention.
Figure 26:
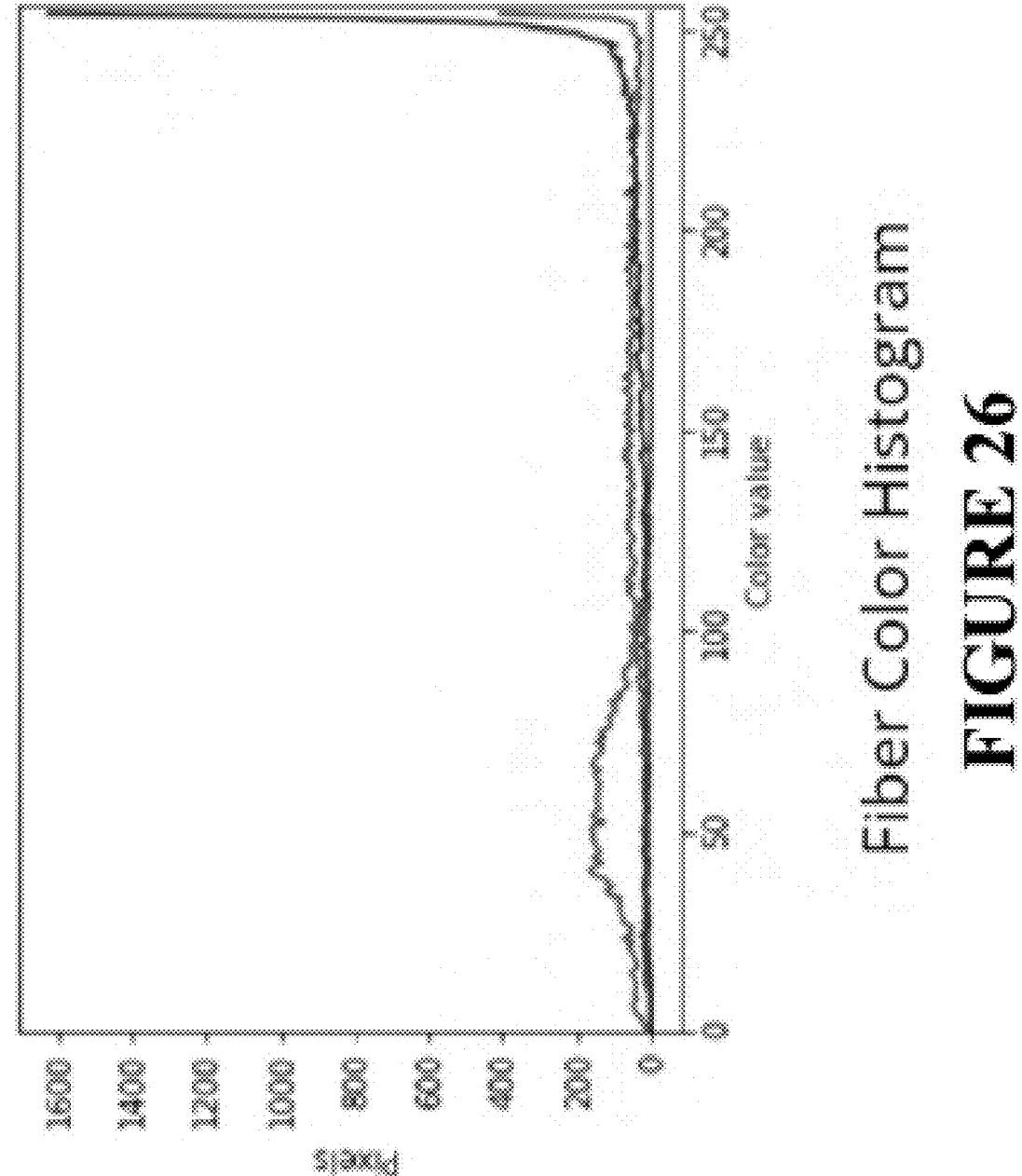
FIG. 26 is a graph showing a fiber color histogram according to aspects of the current invention.
Figure 28:
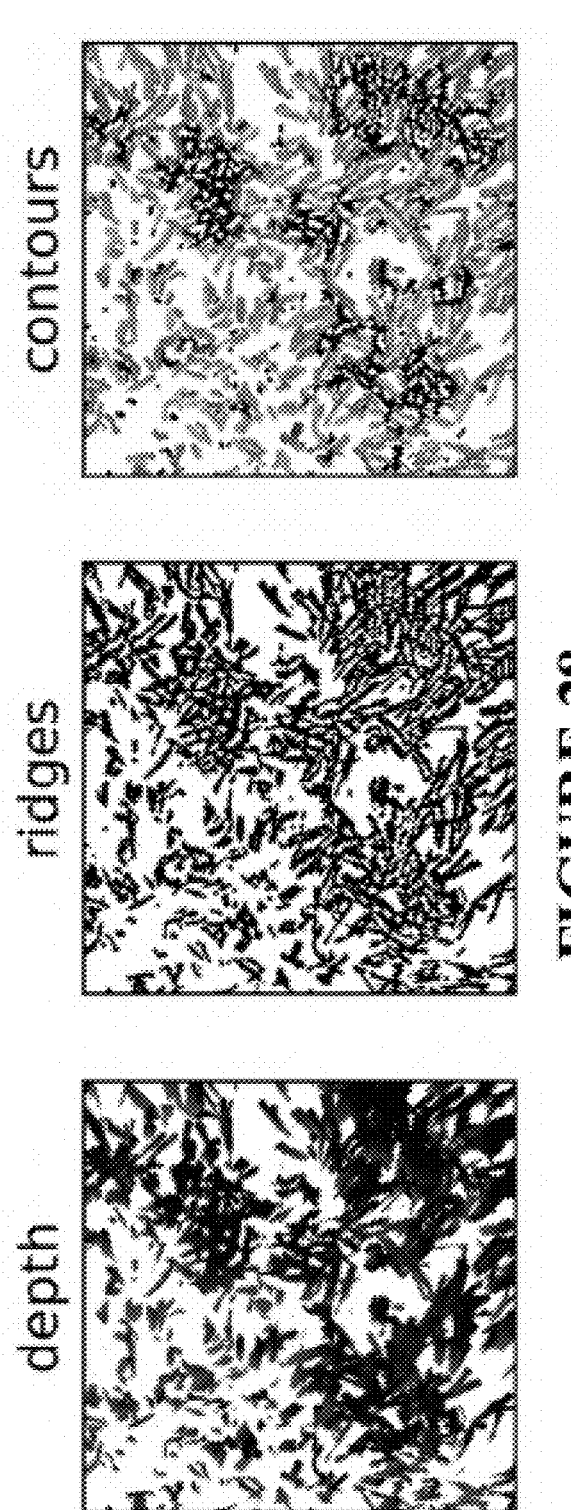
FIG. 28 is a depiction showing a fiber lay analysis (WIP), including depth, ridges, and contours, according to aspects of the current invention.
Figure 29:
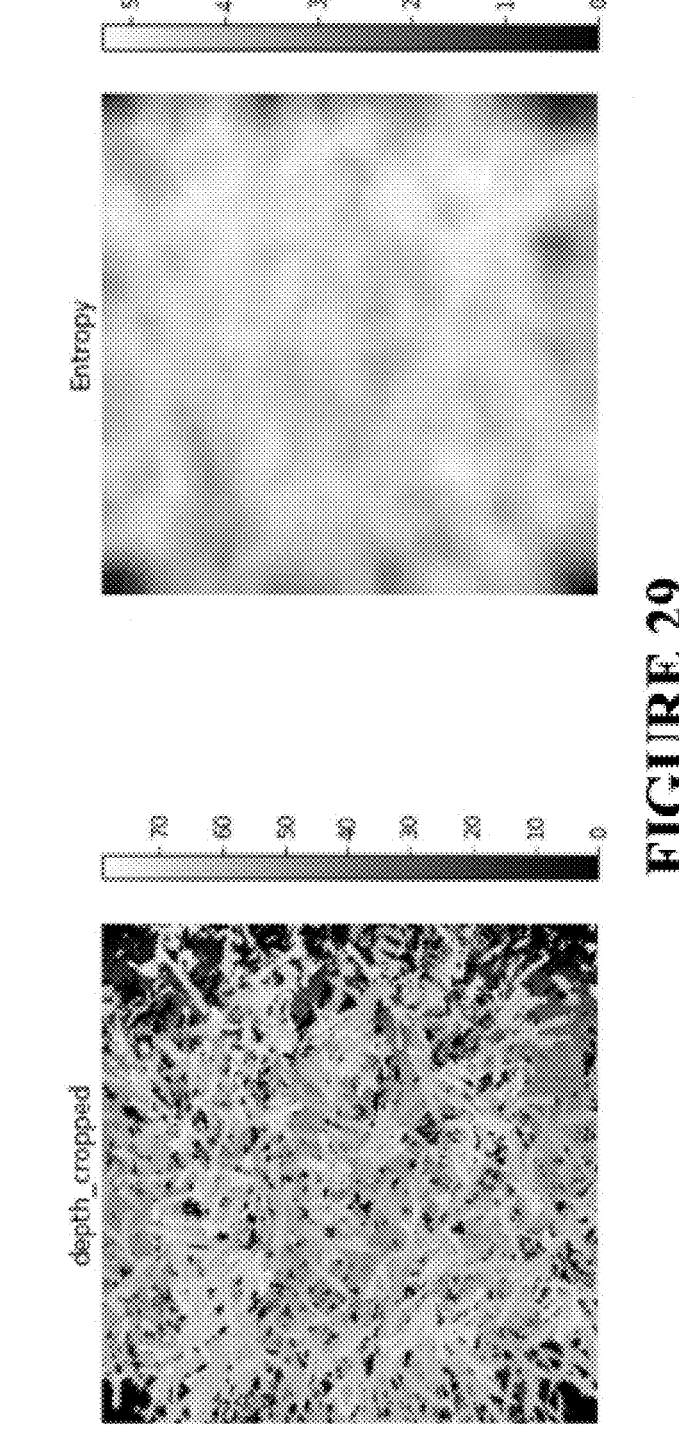
FIG. 29 is a depiction showing regional entropy of fibers according to aspects of the current invention.
Figure 30:
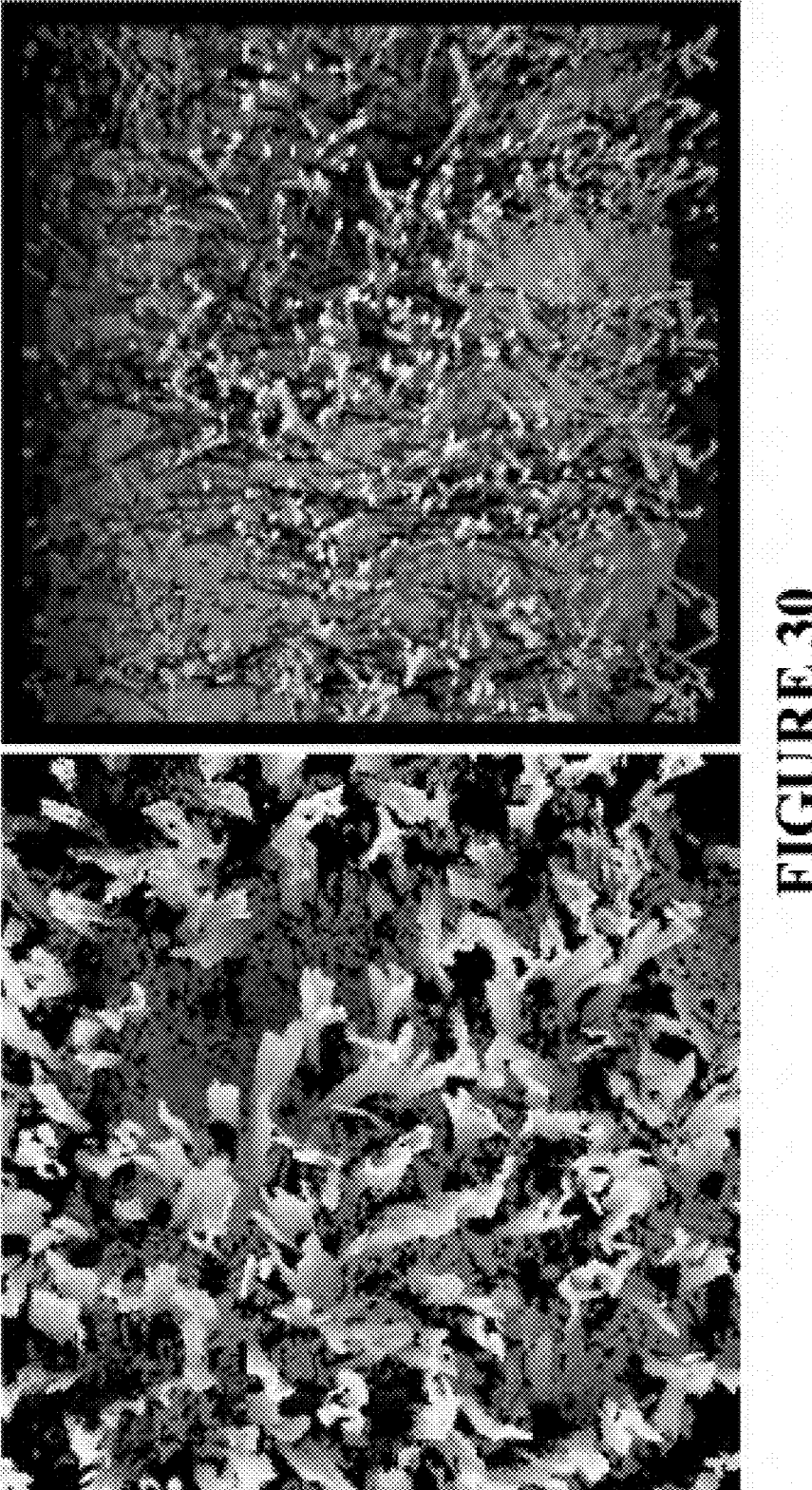
FIG. 30 is a depiction showing a fiber analysis according to aspects of the current invention.
Figure 31:
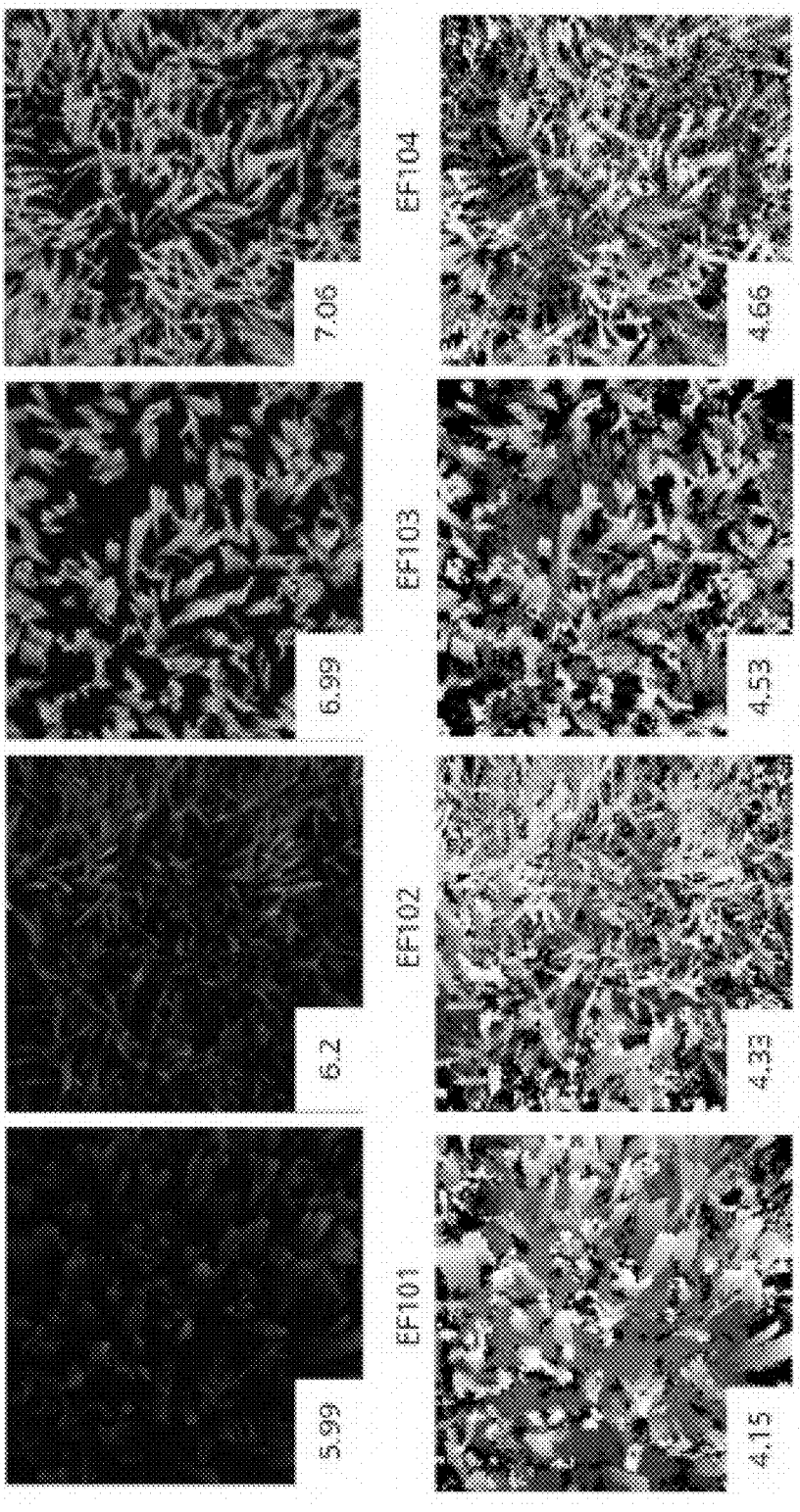
FIG. 31 is a depiction showing a fiber analysis according to aspects of the current invention.
Figure 32:
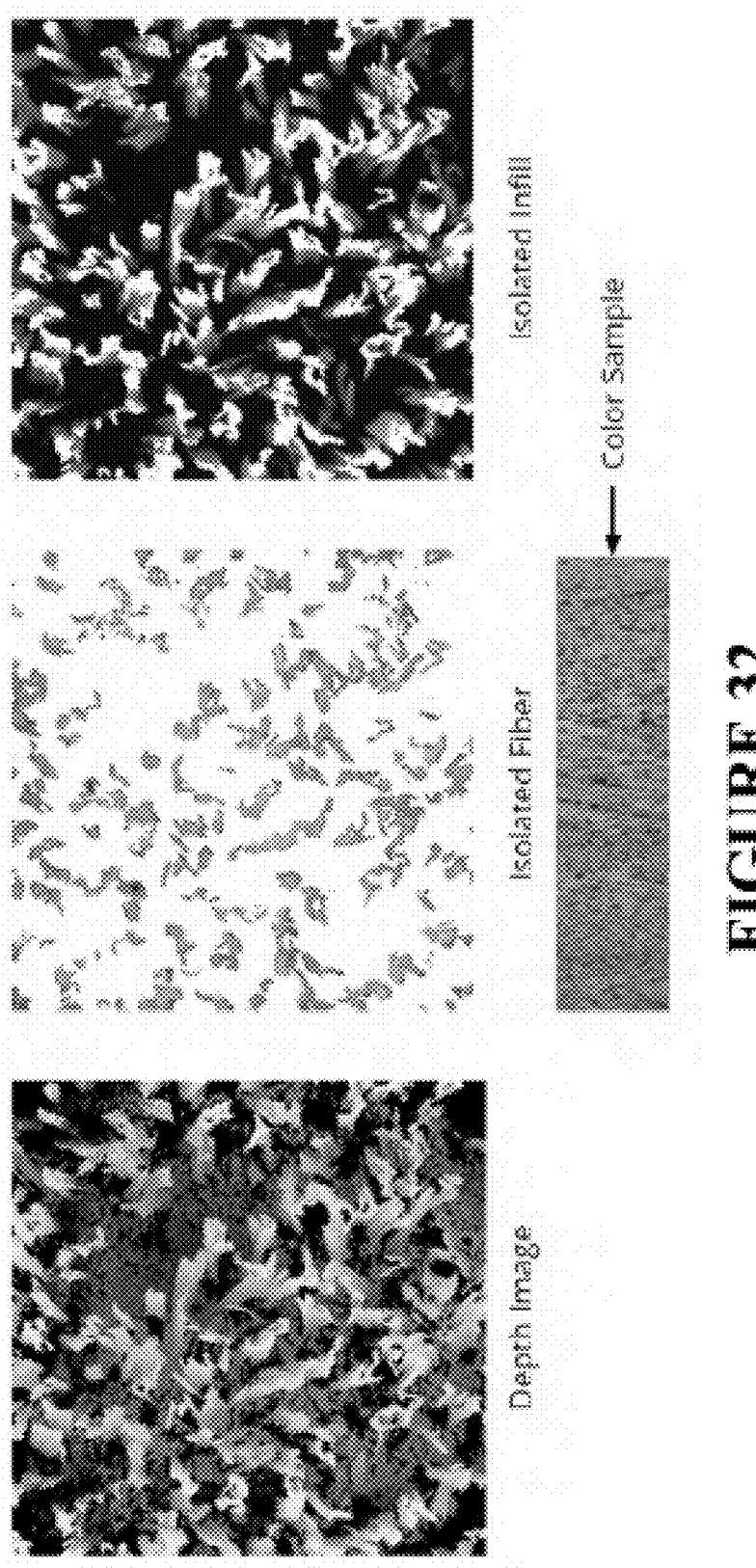
FIG. 32 is a depiction showing a fiber analysis, showing a depth image, an isolation of the fibers, an isolation of the infill, and a color sample according to aspects of the current invention.
Figure 33:
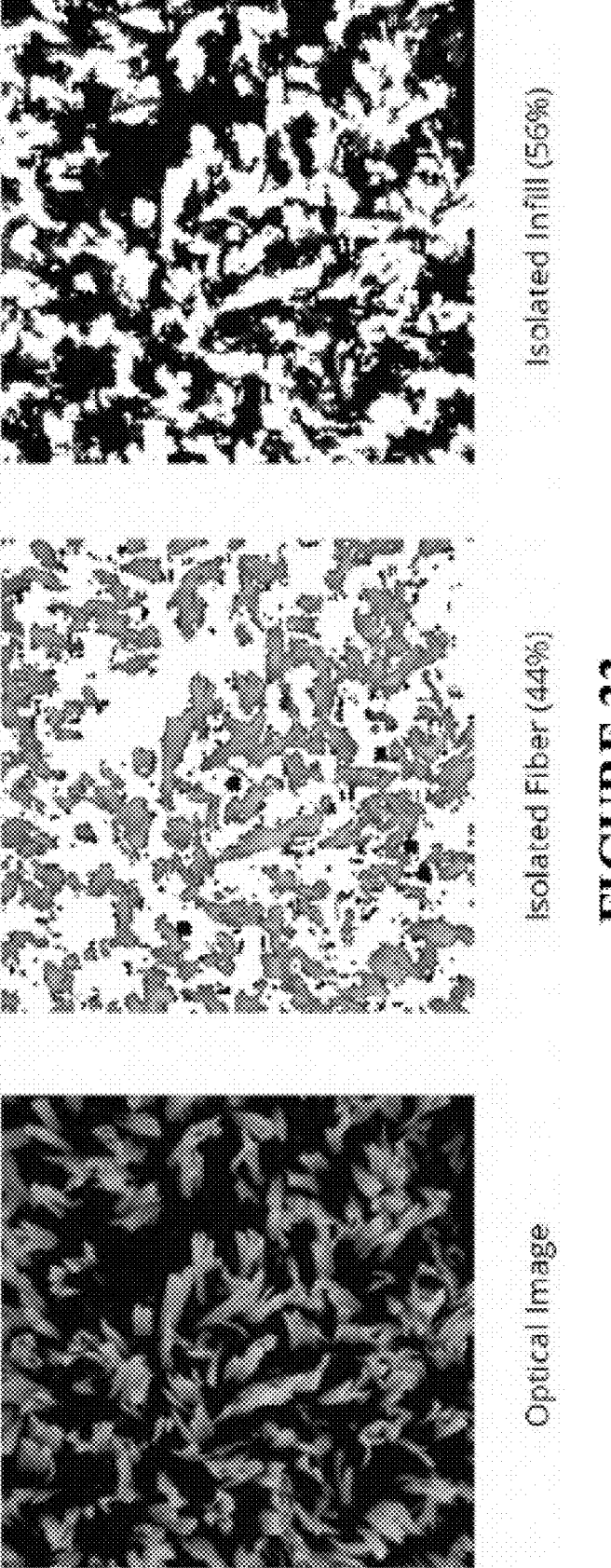
FIG. 33 is a depiction showing a fiber analysis, showing a depth image, an isolation of the fibers, an isolation of the infill, and a color sample according to aspects of the current invention.

Turning to other Figures, FIG. 24 shows a distribution of infill and fiber height analyzed from a depth map of a turf sample, and using a process named fiber mask to isolate individuals components. FIG. 25 shows an analysis of a turf's color palette via analysis of a fiber mask, a process according to the current invention that isolates the fiber component from other elements in the depth map (e.g., infill, dirt). FIG. 26 shows a distribution of pixels for a given color in the turf depth map. FIG. 27 shows a fiber lay direction analysis using blob detection. FIG. 28 shows another aspect of the fiber lay direction analysis using blob detection according to the current invention. FIG. 29 shows image entropy according to aspects of the current invention, which is the measurement of the randomness or state of disorder in the pixels of the depth map, which can be an indicator of turf breakdown. FIG. 30 shows a completed depth map (on the left) and the same on the right, except on the right the individual lasers that contribute to the map are color-coded. In aspects, the lasers fill in each other's shadows (single-color areas) and they all can see the tips of the fibers (white areas). FIG. 31 shows scans and optical images taken from the same camera, and overlayed exactly. In FIG. 31, a range of samples is shown with their optical and depth images. The numbers inlaid at the bottom of each scan/optical image are the total entropy in the image, which can be used as a measurement or a parameter of a measurement. FIG. 32 shows the fiber mask procedure, breaking down different layers of the turf, and isolating components of interest. FIG.

Figure 35:
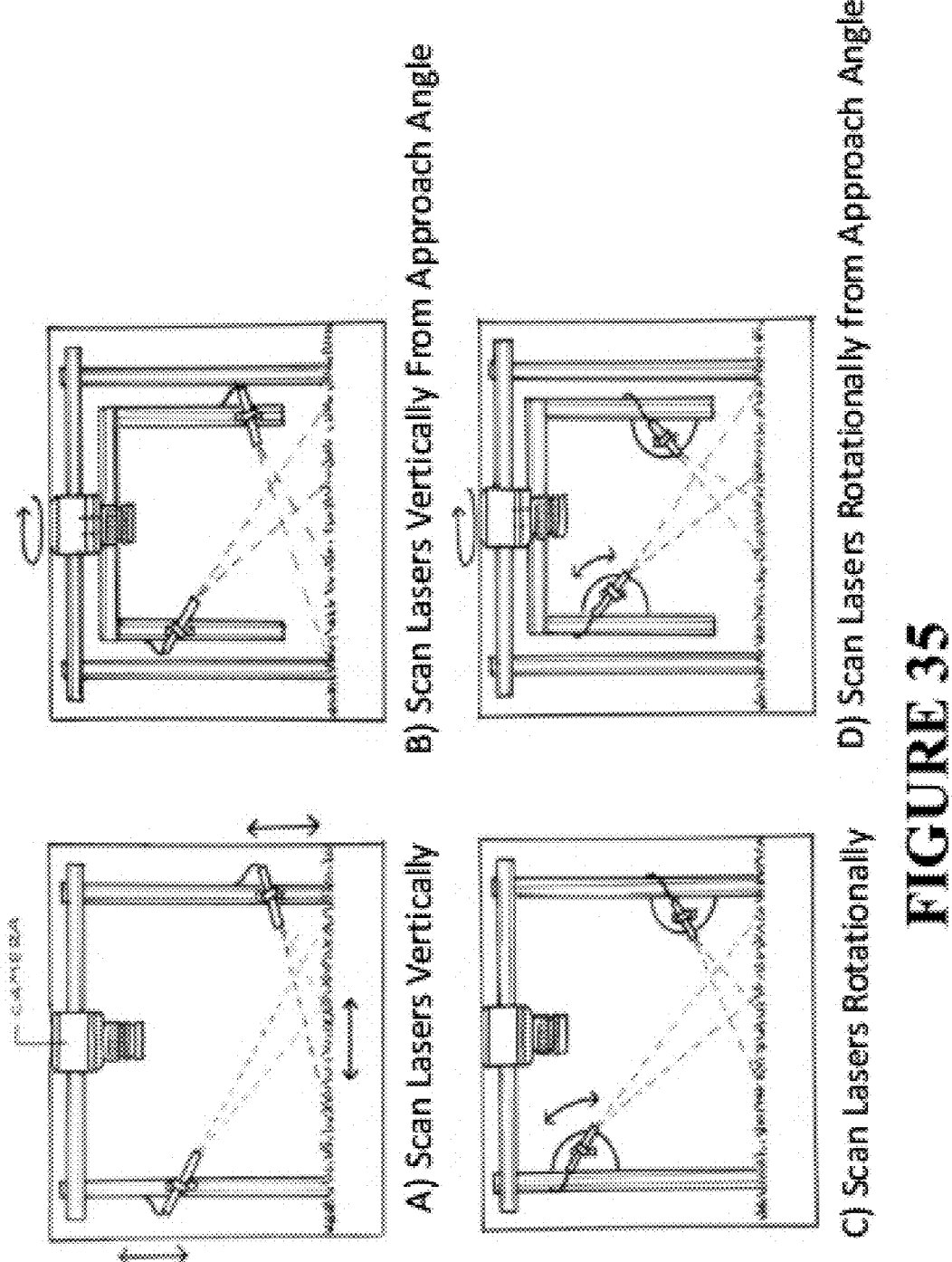
FIG. 35 is a depiction of an embodiment of the current invention.

33 shows the fiber mask procedure, breaking down different layers of the turf, and isolating components of interest. FIG. 34 shows line-of-best-fit equations from scan calibration, for each scanner. These can be used to model where the lasers are in the frame over time for future scans. FIG. 35 shows an embodiment of how a distribution of infill and fiber height is analyzed/determined according to the current invention. In aspect A), the scan lasers move vertically, and in aspect B), the scan lasers move vertically from an approach angle(s). In aspect C), the scan lasers can move rotationally, and in aspect D), the scan lasers can move rotationally from an approach angle(s).

In other embodiments of the invention, files comprising the set of computer-executable instructions may be stored in computer-readable memory on a single computer or distributed across multiple computers or involve a network of remote servers hosted on the internet. In aspects, local, edge, or remote computing possibilities are used to store, manage, and process data. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general-purpose computer, a special-purpose computer, or other programmable data processing apparatus to produce a particular machine, such that the one or more computers or devices are instructed and configured to carry out the calculations, processes, steps, operations, algorithms, statistical methods, formulas, or computational routines of this disclosure. The computer or device performing the specified calculations, processes, steps, operations, algorithms, statistical methods, formulas, or computational routines of this disclosure may comprise at least one processing element such as a central processing unit (i.e., processor) and a form of computer-readable memory which may include random-access memory (RAM) or read-only memory (ROM). The computer-executable instructions can be embedded in computer hardware or stored in the computer-readable memory such that the computer or device may be directed to perform one or more of the calculations, steps, processes, and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g., software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database.

The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI) which may be used in conjunction with the computer-executable code and electronic databases. The graphical user interface may allow a user to perform these tasks through the use of text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

As used herein, the term "about" refers to plus or minus 5 units (e.g., percentage) of the stated value.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, the term "substantial" and "substantially" refers to what is easily recognizable to one of ordinary skill in the art.

It is to be understood that the phraseology and terminology employed herein is not to be construed as limiting and are for descriptive purpose only.

It is to be understood that while certain of the illustrations and figure may be close to the right scale, most of the illustrations and figures are not intended to be of the correct scale.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

The invention claimed is:

1. A computer-implemented method for inspecting a ground surface, the method comprising:

capturing, via at least one camera, an optical image of the ground surface, wherein the ground surface includes at least one of: grass, artificial turf, infill, and dirt, and the optical image includes at least one of a photographic image and a video image;

capturing, via at least one laser, a three-dimensional ("3D") depth scan of the ground surface; and via a computing processor, in response to executable instructions:

electronically combining the optical image of the ground surface and the 3D depth scan of the ground surface;

sampling or recording one or more color, one or more depth, or a combination of the one or more color and the one or more depth, in a portion of or all of the optical image, the 3D depth scan, or a combination of the optical image and the 3D depth scan;

creating a mask using the sampling or recording of the one or more color, the one or more depth, or the combination of the one or more color and the one or more depth, in the portion or all of the optical image, the 3D depth scan, or a combination of the optical image and the 3D depth scan;

using the mask to distinguish (a) fiber of at least one of the grass or the artificial turf from (b) at least one of the infill or the dirt; and determining, using the optical image or the 3D depth scan, one or more lay direction of the grass or the artificial turf, in both a two-dimensional optical space and a 3D depth space.

2. The computer-implemented method of claim 1, further comprising characterizing a geometry of the fiber of the artificial turf or a morphology of the fiber of the grass to measure or analyze at least one of usage, wear, and tear, of the artificial turf or the grass.

3. The computer-implemented method of claim 1, wherein the measurement or the analysis are replicable and reproducible.

4. The computer implemented method of claim 1, wherein the measurement or the analysis are to differentiate between the grass and the dirt.

5. The computer-implemented method of claim 1, wherein the measurement or the analysis are to at least one of:

differentiate green grass from dormant grass, thatch, or a plant material of a different color from the grass;

differentiate grass blades from another morphological structure chosen from one or more of: stolon, rhizome, crown, seedhead, or a morphological structure having at least one of a different shape or color than the grass blades; or differentiate the artificial turf from the infill.

6. The computer-implemented method of claim 5, wherein the infill is chosen from at least one of: rubber crumb, polymeric infill, sand, organic particulate material, or inorganic particulate material.

7. The computer-implemented method of claim 1, wherein the at least one camera is a high-speed camera.

8. The computer-implemented method of claim 7, wherein the high-speed camera is capable of taking over 300 frames per second.

9. The computer-implemented method of claim 1, further comprising at least one of machine learning visual recognition or data synchronization.

10. The computer-implemented method of claim 1, further comprising providing for at least one of: identifying foreign objects in or on the ground surface, determining safety for playing a sport on the ground surface, performing one or more ground surface evenness test, or determining grass or artificial turf density.

11. The computer-implemented method of claim 1, further comprising providing a user interface capable of generating or presenting at least one of data, data analysis, or data interpretation.

12. The computer-implemented method of claim 1, wherein the computer processor is located on a same apparatus also including the at least one camera and the at least one laser, or wherein the computer processor is located remote from an apparatus including the at least camera and the at least one laser, and wherein the computer processor provides a scoring or ranking of the ground surface.

13. The computer-implemented method of claim 1, wherein two or more of the at least one laser are different colors.

14. The computer-implemented method of claim 1, wherein a first laser of the at least one laser is a first color and a second laser of the at least one laser is a second color.

15. The computer-implemented method of claim 1, wherein a plurality 3D depth scans are partially or completely overlapping or overlaid relative to one another.

16. The computer-implemented method of claim 1, wherein:

the at least one laser is reflected off at least one mirror and oriented orthogonally or substantially orthogonally to the at least one camera;

a first laser of the at least one laser is oriented orthogonal to a second laser of the at least one laser;

a first laser and a second laser of the at least one laser are oriented orthogonal to one another, providing for scanning from a plurality of angles, which accounts for directionality problems or abnormalities related to the ground surface; and/or a first laser and a second laser of the at least one laser are oriented orthogonal to one another, and wherein the orthogonal orientation at least one of: (a) cancels out shadows in a depth map, and (b) senses behind taller features that block one or more beam from the first laser or the second laser scanning from other angles.

17. The computer-implemented method of claim 1, further comprising providing one or more geared step motor to at least one of:

direct the at least one laser across the ground surface by at least one of aligning or directing one or more steering mirror for the at least one laser;

direct one or more beams from the at least one laser to swipe or scan across the ground surface, which generates a scan and depth map; or direct one or more beams from the at least one laser to swipe or scan across the ground surface, which generates the 3D depth scan.

18. The computer-implemented method of claim 1, further comprising providing a first depth map of the fiber of the at least one of the grass or the artificial turf, and a second depth map of the at least one of the infill or the dirt, which are used to at least one of:

extract data about evenness of any one or more of the grass, the artificial turf, the infill, or the dirt, together or compared against one another;

extract data about coverage of the at least one of the grass, the artificial turf, the infill, or the dirt; or extract data comparing how much infill or dirt is exposed as compared to the grass or the artificial turf.

19. The computer-implemented method of claim 1, further comprising providing a depth map of the fiber of the at least one of the grass or the artificial turf, which is used to extract data regarding geographical characteristics, morphological characteristics, or both, of at least one of the fiber of the artificial turf, the fiber of the grass, or a fiber of a grass blade.

20. The computer-implemented method of claim 1, further comprising using at least one of the optical image and the 3D depth scan, to provide a statistical sampling of a three-dimensional orientation at least one of the grass and the artificial turf.

21. The computer-implemented method of claim 1, further comprising at least one of:

(a) compiling test results and displaying them via a user interface;

(b) comparing test results against hard-coded or server-based baseline data to score the test results against;

(c) retrieving historical results from tests and comparing the historical results with baseline hard-coded data, and/or comparing the historical results with new test results;

(d) evaluating and scoring geographical consistency of the ground surface by registering more than one test with one or more location using a Global Positioning System and analyzing test results from multiple locations using at least one of correlation, coefficient of variation, standard error, or standard deviation, to assess variability;

(e) flagging or recommending intervention if the ground surface may be dangerous or of poor quality; or (f) one or more of collecting, registering, synchronizing, retrieving, or analyzing metadata related to the ground surface.

22. The computer-implemented method of claim 1, further comprising using the mask to isolate two components of the ground surface for measuring or determining:

a distribution of artificial turf height from a ground surface, height of the artificial turf over infill, or combinations thereof;

a variation of detected heights;

a distribution of categories represented in the optical image;

existence of one or more patch of exposed infill or dirt;

tape width, tape wear, or combinations thereof, using blob detection or filtered line detection;

artificial turf lay using orientation of detected blobs and a perpendicular direction to height gradient;

color distribution of the grass;

detection of grass color;

detection of paint, paint color, or both, on any one or more of the grass, the artificial turf, the infill, or the dirt;

distribution clusters of color in the optical image; and/or development of at least one of grass species or seasonality benchmarks, including at least one of change in color, morphology, or quality decline due to disease or pests.

23. The computer-implemented method of claim 1, further comprising presenting one or more surface feature to a user as at least one of a single metric, a distribution, an average, or distributions over time.

24. A computer-implemented method for inspecting a ground surface, the method comprising:

capturing, via at least one camera, an optical image of the ground surface, wherein the ground surface includes at least one of: grass, artificial turf, infill, and dirt, and the optical image includes at least one of a photographic image and a video image;

capturing, via at least one laser, a three-dimensional ("3D") depth scan of the ground surface; and via a computing processor, in response to executable instructions:

electronically combining the optical image of the ground surface and the 3D depth scan of the ground surface;

sampling or recording one or more color, one or more depth, or a combination of the one or more color and the one or more depth, in a portion of or all of the optical image, the 3D depth scan, or a combination of the optical image and the 3D depth scan;

creating a mask using the sampling or recording of the one or more color, the one or more depth, or the combination of the one or more color and the one or more depth, in the portion or all of the optical image, the 3D depth scan, or a combination of the optical image and the 3D depth scan;

using the mask to distinguish (a) fiber of at least one of the grass or the artificial turf from (b) at least one of the infill or the dirt;

electronically measuring or analyzing, or both electronically measuring and analyzing, at least one of the grass, the artificial turf, the infill, and the dirt; and wherein the one or more color comprises two different colors, which can be automatically selected based on dispersion from the at least one laser depending on at least one of ground surface color and ground surface sheen.

* * * * *